(12) United States Patent
Ferguson et al.

(10) Patent No.: US 7,404,640 B2
(45) Date of Patent: Jul. 29, 2008

(54) MONITORING BLOOD FLOW IN THE RETINA USING A LINE-SCANNING LASER OPHTHALMOSCOPE

(75) Inventors: R. Daniel Ferguson, Melrose, MA (US); Daniel X. Hammer, Andover, MA (US)

(73) Assignee: Physical Sciences, Inc., Andover, MA (US)

( * ) Notice: Subject to any disclaimer, the term of this patent is extended or adjusted under 35 U.S.C. 154(b) by 441 days.

(21) Appl. No.: 11/043,028

(22) Filed: Jan. 25, 2005

(65) Prior Publication Data
US 2005/0254008 A1    Nov. 17, 2005

Related U.S. Application Data

(63) Continuation-in-part of application No. 10/864,081, filed on Jun. 9, 2004, now Pat. No. 7,284,859, which is a continuation of application No. 10/171,883, filed on Jun. 14, 2002, now Pat. No. 6,758,564.

(51) Int. Cl.
   *A61B 3/10* (2006.01)
(52) U.S. Cl. ..................................... 351/221
(58) Field of Classification Search ............... 351/205, 351/206, 221; 600/407, 473, 476; 606/4, 606/5; 356/601, 606, 607, 608; 250/559.03, 250/559.04, 669.22, 69.22
See application file for complete search history.

(56) References Cited

U.S. PATENT DOCUMENTS

| 4,579,430 | A  | * | 4/1986 | Bille ........................... 351/206 |
| 6,275,718 | B1 | * | 8/2001 | Lempert ..................... 600/407 |
| 6,305,804 | B1 | * | 10/2001 | Rice et al. .................... 351/221 |
| 7,113,817 | B1 | * | 9/2006 | Winchester et al. ......... 600/476 |

OTHER PUBLICATIONS

Kobayashi et al., "Confocal scanning laser ophthalmoscope with a slit aperature," J. Phys. Sci. Technol. 2, 287-292 (1991).
Heacock et al., "Imaging of the choroid with the scanning slit laser ophthalmoscope (SSLO)," SPIE vol. 3591, 456-464 (1999).
Hammer et al., "Compact scanning laser ophthalmoscope with high-speed retinal tracker," vol. 42, No. 22, 4621-4632 (2003).

* cited by examiner

*Primary Examiner*—George Manuel
(74) *Attorney, Agent, or Firm*—Proskauer Rose LLP

(57) ABSTRACT

Real time, high-speed image stabilization with a retinal tracking scanning laser ophthalmoscope (TSLO) enables new approaches to established diagnostics. Large frequency range (DC to 19 kHz), wide-field (40-deg) stabilized Doppler flowmetry imaging is described for human subjects. The fundus imaging method is a quasi-confocal line-scanning laser ophthalmoscope (LSLO). The retinal tracking system uses a confocal reflectometer with a closed loop optical servo system to lock onto features in the ocular fundus and automatically re-lock after blinks. By performing a slow scan with the laser line imager, frequency-resolved retinal perfusion and vascular flow images can be obtained free of eye motion artifacts.

27 Claims, 23 Drawing Sheets

Imaging System

Point Imaging / scanning

USAF Target

USAF Target

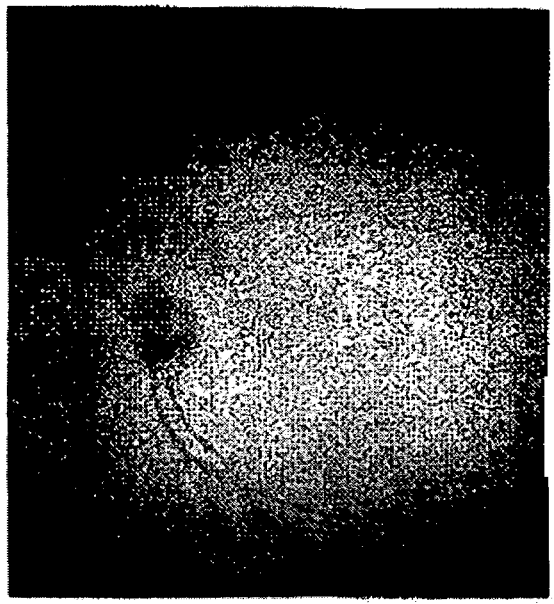
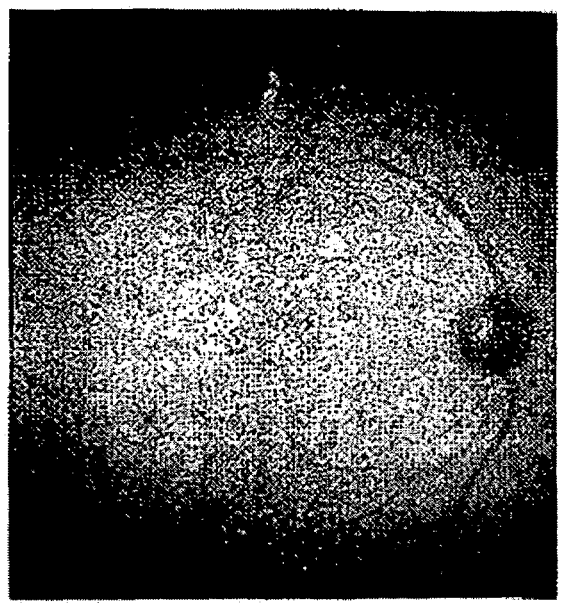
FIG. 7A  FIG. 7B
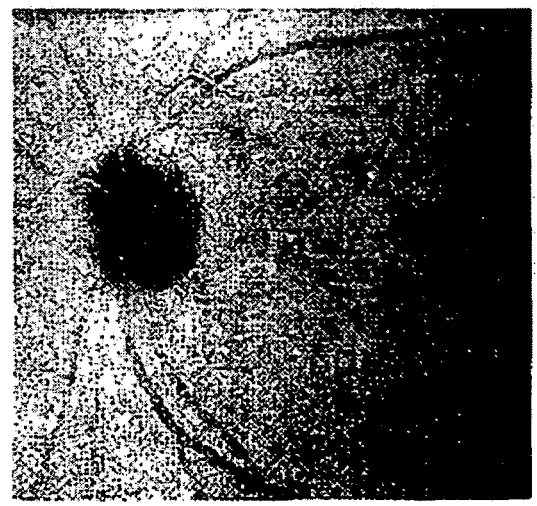
FIG. 8
PRIOR ART

MONITORING BLOOD FLOW IN THE RETINA USING A LINE-SCANNING LASER OPHTHALMOSCOPE

CROSS-REFERENCE TO RELATED APPLICATION

This application is a continuation-in-part of U.S. patent application Ser. No. 10/864,081 filed Jun. 9, 2004, which is a continuation of U.S. patent application Ser. No. 10/171,883 filed on Jun. 14, 2002, both of which are owned by the assignee of the instant application and the disclosures of which are incorporated herein by reference in their entireties.

GOVERNMENT RIGHTS

This invention was made with government support under Contract No. 1 R43 EY11819-01A1 awarded by the National Institute of Health/National Eye Institute. The government may have certain rights in the invention.

FIELD OF THE INVENTION

This invention relates generally to systems and methods for examining eyes. More particularly, the invention relates to systems and methods that employ scanned lines of light for examining eyes and monitoring blood flow in the retina.

BACKGROUND OF THE INVENTION

The retina is among the most highly vascularized and metabolically active tissues in the body. Like the central nervous system of which it is a part, it is also susceptible to ischemic injury. Degenerative diseases of the eye often have either hemodynamic consequences or causes, though many mechanisms remain unknown. Improved blood flow imaging diagnostics for retinal circulation and perfusion can aid the detection and management of eye disease, and research on retinal function and metabolism.

The retinal circulation apparent in images generated by scanning laser ophthalmoscopy (SLO) originates from the central retinal artery that passes through the optic nerve head before branching into superior, inferior, nasal, and temporal arteries, into many smaller vessels, and ultimately, into capillary networks. The underlying choroidal vessels and choriocapillaris beneath the retinal pigment epithelium (RPE) account for approximately 90% of the blood flow nourishing the retina. While rapid flow in the retinal vascular tree is readily visualized, the perfusion of the retina through the micro-vasculature on both sides of the RPE is critically important. For eye diseases such as diabetic retinopathy, macular degeneration, and glaucoma, these structures exhibit early flow defects or the growth of new vessels triggered by metabolic distress and other factors.

Both the retinal and choriodal vessel diameters range from ~5 µm (in the retinal capillary bed and choriocapillaris) to ~0.4 mm (major vessels). Flow rates range from local quasi-isotropic perfusion rates of tens of µm/s in the capillaries to pulsatile values of several cm/s in the arteries. This range of dimensions and flow parameters presents an extremely demanding diagnostic problem in terms of spatial resolution, field of view, and dynamic range. Dye angiography is a powerful tool for global visualization of retinal vessel topology, occlusions and, uniquely, leakage. Fluorescein and indocyanine green (ICG) dyes have different properties that emphasize different aspects of vascular physiology. However, at present, early transit phase dye angiography of both types can provide at best only a fleeting glimpse of dynamic flow characteristics. Few methods accomplish dynamic blood flow imaging non-invasively (i.e., without dyes); fewer still quantitatively; and none with the wide field, high resolution, and dynamic range to characterize retinal hemodynamics globally. Reproducibility is essential for longitudinal studies, and also for sensitive detection of functional correlations with local neuronal activity or pharmacological effects. In short, despite decades of research and the introduction of several advanced systems for measurement of blood flow, retinal blood flow Doppler imaging diagnostics have not yet achieved the clinical prominence that retinal biology would seem to justify.

When imaging biological tissues with lasers, the phenomenon of speckle is a necessary consequence of coherent illumination. The superposition of scattered photons for an extended source produces a net wavefront at the receiving aperture that varies in amplitude and phase. For imaging instruments whose signal-to-noise ratio is well above the shot noise limit, speckle can be a dominant source of the large fluctuations in apparent reflectivity and the granularity in captured images (depending on the degree of confocality). A stationary ensemble of scatterers can produce a stationary speckle pattern. Such variations are not intrinsic reflectivity variations, and so from a static imaging viewpoint, can be regarded as noise, with concomitant reduction of image contrast and spatial resolution. When particles in motion are of interest, however, the scattered light also has imposed Doppler frequency shifts dependent upon the scattered wave-vectors and velocities of the particles. The frequency content of the imaged light can be measured and velocities inferred. In this sense, in living biological tissue, speckle can be regarded as a contrast agent enabling the visualization of dynamic processes.

Speckle interferometry and its related imaging technologies can exploit the temporal characteristics of fluctuations that contain information about the motion of particles within an optically probed or imaged volume. The DC or zero frequency component of the temporal spectrum at an image pixel can include the time-averaged power during the observation, and therefore asymptotically, the intrinsic incoherent reflectivity or the "speckle-free" image. The AC component can include quantitative measures related to particle number density and velocity distributions within the probed volume element (voxel).

Multiple scatterers within image volumes can give rise to some complex and often counter-intuitive characteristics for Doppler signals. Red blood cells are strongly forward scattering in the near infrared, and most of the scattered light per interaction falls within a sharply peaked cone with ~6 deg half angle. The result can be a distribution of Doppler frequencies even for a single well-defined velocity vector. Direct backscatter from flowing blood is generally a weak component of the signal, so the usual conception of the Doppler signal can be misleading. Mainly, light forward scattered by blood is subsequently backscattered by denser tissues. This dual-scatter enables velocities perpendicular to the incident beam to contribute to the Doppler signal, but can result in Doppler signals that have ambiguous spatial origin. At the largest scales of arteries and veins in, fore example, the retina, the velocities are large with a single well-defined direction. At the capillary or perfusion scale, velocities are small, perhaps with multiple flow directions within a single voxel. Multiple light scattering can cause these fine scales to lose contrast in flow images based upon Doppler frequency shifts. However, the total Doppler signal power per unit of imaged moving tissue volume is approximately preserved.

Some of the first applications of Doppler methods to retinal blood flow diagnostics used a single laser beam that was focused on the retina, and the flow in retinal vessels and capillary perfusion were found to be measurable and quantifiable with laser Doppler flowmetry. Later, two imaging approaches emerged using CCD fundus images (laser speckle imaging or flowgraphy) and flying-spot confocal SLO devices such as scanning laser Doppler flowmetry (e.g., Heidelberg Retinal Flowmeter, HRF). Concurrently, color Doppler optical coherence tomography (OCT) or optical Doppler tomography (ODT) was found to provide local anatomical detail with velocity information when blood moves parallel to the probe beam. Such measurements can be difficult to interpret for complex vessel topology. Most recently, the remarkable capabilities of high-speed, spectral domain ODT (SDODT) for blood flow measurement have been described. The improvement in retinal flow visualization has been considerable. However, all of these approaches trade resolution, field-of-view, dynamic range, velocity component sensitivity and Doppler frequency range against scan speed and system noise. The motion of the eye, the cardiac and respiratory rhythms and other effects render the lowest frequencies virtually uninterpretable. Low data rates and high-frequency aliasing render the highest flows inaccessible and/or inaccurate.

Many scanning imaging technologies can suffer from practical limitations in the living eye as well at eye-safe light levels, e.g., scan areas or volumes and scan times are restricted by eye motions or other registration issues that corrupt data and are generally not correctable by post-processing. In other words, at present, almost all scanning imaging operations must fit within a relatively brief window in time—for example, on the order of a second, approximately the mean time between small saccades. This severely impacts the size of the measured fields and the trade-offs that need to be made in data quality. The resulting difficulties of flow quantification, velocity range, sensitivity, dynamic range, and field of view have not yet been overcome by the prior art, especially for correlation of precise information about local anatomical features with the wide-field angiographic data familiar to clinicians.

SUMMARY OF THE INVENTION

The invention, in one embodiment, features a line-scanning laser ophthalmoscope (LSLO) in conjunction with a high-speed retinal tracking system, which yields a tracking scanning laser ophthalmoscope (TSLO). The LSLO can image the retina by scanning a line of laser light, which can be confocal, with a linear sensor array or linear array detector. In one embodiment, the LSLO is therefore neither a true SLO nor a fundus camera, while possessing some of the advantages of both. These include efficient rejection of stray light and high speed read-out with no scanning on one axis (e.g., along the line). For each of these methods, light scattered from (z) planes above and below the focal plane can contribute to the image signals. For the SLO, the out-of-focus contributions fall off as $1/z^2$, which provides its intrinsic optical sectioning capability. For the fundus camera with flood illumination, out-of-focus contributions (no z-dependence) are generally not rejected, which can account for its poor contrast. Finally, the LSLO can exhibit an approximate $1/z$ dependence in its sensitivity to out-of-focus light, which can be regarded as an intermediate behavior or as "quasi-confocal."

In one embodiment, the TSLO is configured for wide-field, large dynamic range stabilized Doppler flowmetry (SDF). Because of the high fidelity retinal tracking function, most eye motion artifacts can be eliminated, and the temporal spectrum at each pixel can be obtained. High contrast, low-noise, frequency-resolved retinal microvasculature and perfusion maps can then be visualized and recorded in a new dye-free angiography mode. With the novel imaging approach described below and advanced user interface features, the accessible Doppler frequency range for blood flow speeds can be significantly expanded both upwards and downwards, while eliminating confounding imaging artifacts and some limitations of earlier methods.

The addition of real time, high-speed retinal image stabilization is not merely a convenience. While retinal tracking can simplify some current clinical diagnostic protocols, and can reduce or eliminate registration issues by stabilizing relative to fixed retinal landmarks, its real contribution is potentially more fundamental. Tracking can enable the duration of any given scan or scan sequence to be effectively indefinite.

The familiar continuous spatial scan dimensions are the A-scan (z axis), B-scan (x or y-axis), and C-scan (y or x-axis). Precision stabilization robustly adds a new scan dimension to clinically practical diagnostics: the T-scan (the time axis). Any spatial and temporal scan sequence can be specified with combinations of these: e.g., a BC scan is a xy-plane, while a BT scan is a single line re-scanned in time.

In one aspect, the invention features a method of monitoring blood flow in a retina. The method includes illuminating the retina with a line of light at a first position and a second position, and recording a first plurality of images of the retina at the first position and a second plurality of images of the retina at the second position. Each of the first plurality of images is recorded at a first set of successive time periods to form a first spatial-temporal image plane, and each of the second plurality of images is recorded at a second set of successive time periods to form a second spatial-temporal image plane. The first spatial-temporal image plane and the second spatial-temporal image plane are combined to form a three-dimensional image of the retina. The temporal dimension represents the flow of blood in the retina.

In one embodiment, each of the spatial-temporal image planes has N spatial pixels and N temporal pixels. The method can also include illuminating the retina with a line of light at N positions to form N spatial-temporal image planes. In one embodiment, the method includes combining the N spatial-temporal image planes to form an image cube of the retina with dimensions of N×N×N. In one embodiment, a respective plurality of images are confocally received with a linear array detector light reflected from the portion of the retina illuminated with the line of light.

The method can also include performing a Fourier transform of the three-dimensional image of the retina to extract a power spectrum of each image pixel. The power spectrum can include an AC portion representing blood flow and a DC portion representing average image brightness. Normalizing the power spectrum by the DC values to can remove variability across a respective plurality of images due to intensity of the line of light or reflectivity of an imaged volume of tissue. In various embodiments, the method includes binning portions of the power spectrum according to a frequency range (e.g., a low frequency bin represents perfusion through the micro-vasculature of the retina, a middle frequency bin represents blood flow in small retinal vessels, or a high frequency bin represents blood flow in large retinal vessels.) A plurality of frequency bins can be combined to form a video of blood flow and vessel pattern.

In one embodiment, the binned portions of the power spectrum are scaled. The binned portions can be scaled to form a normalized spectrum to compare blood flow in a first patient and blood flow in a second patient. The binned portions can also be scaled to form a normalized stretched spectrum to compare blood flow in a patient at a first time and blood flow in the same patient at a second time.

In another aspect, the invention provides an apparatus for monitoring blood flow in a retina. The apparatus includes a retinal tracking device for locking onto a feature of the retina, and a line-scanning laser ophthalmoscope for illuminating the retina with a line of light at a first position and at a second position. The line-scanning laser ophthalmoscope includes a linear array detector for confocally receiving a first plurality of images of the retina at the first position versus a first set of successive time periods and a second plurality of images of the retina at the second position for a second set of successive time periods. The apparatus also includes a processor for forming a first spatial-temporal image plane from the first plurality of images of the retina at the first position for the first set of successive time periods, forming a second spatial-temporal image plane from the second plurality of images of the retina at the second position versus the second set of successive time periods, and combining the first spatial-temporal image plane and the second spatial-temporal image plane to form a three-dimensional image of the retina. The temporal dimension represents the flow of blood in the retina.

In one embodiment, the retinal tracking device locks a tracking beam onto a retinal feature and processes the back-reflected signal from the tracking beam to stabilize the line-scanning laser ophthalmoscope. The retinal tracking device can track at a rate that exceeds the maximum rate of motion of an eye (e.g., having a bandwidth of greater than 1 kHz). In one embodiment, the retinal tracking device improves the resolution of the line-scanning laser ophthalmoscope.

In yet another aspect, the invention features an apparatus for monitoring blood flow in a retina. The apparatus includes a means for illuminating the retina with a line of light at a first position and a second position, and a means for recording a first plurality of images of the retina at the first position and a second plurality of images of the retina at the second position. Each of the first plurality of images is recorded at successive time periods to form a first spatial-temporal image plane, and each of the second plurality of images is recorded at a respective time period to form a second spatial-temporal image plane. The apparatus also include a means for combining the first spatial-temporal image plane and the second spatial-temporal image plane to form a three-dimensional image of the retina. The temporal dimension represents the flow of blood in the retina.

Other aspects and advantages of the invention will become apparent from the following drawings, detailed description, and claims, all of which illustrate the principles of the invention, by way of example only.

BRIEF DESCRIPTION OF THE DRAWINGS

The advantages of the invention described above, together with further advantages, may be better understood by referring to the following description taken in conjunction with the accompanying drawings. The drawings are not necessarily to scale, emphasis instead generally being placed upon illustrating the principles of the invention.

FIG. 7 shows forty degree field LSLO images in the left and right eyes of a human subject, according to principles of the invention.

FIG. 8 shows a standard SLO image of the prior art.

DESCRIPTION OF THE INVENTION

Figure 1:
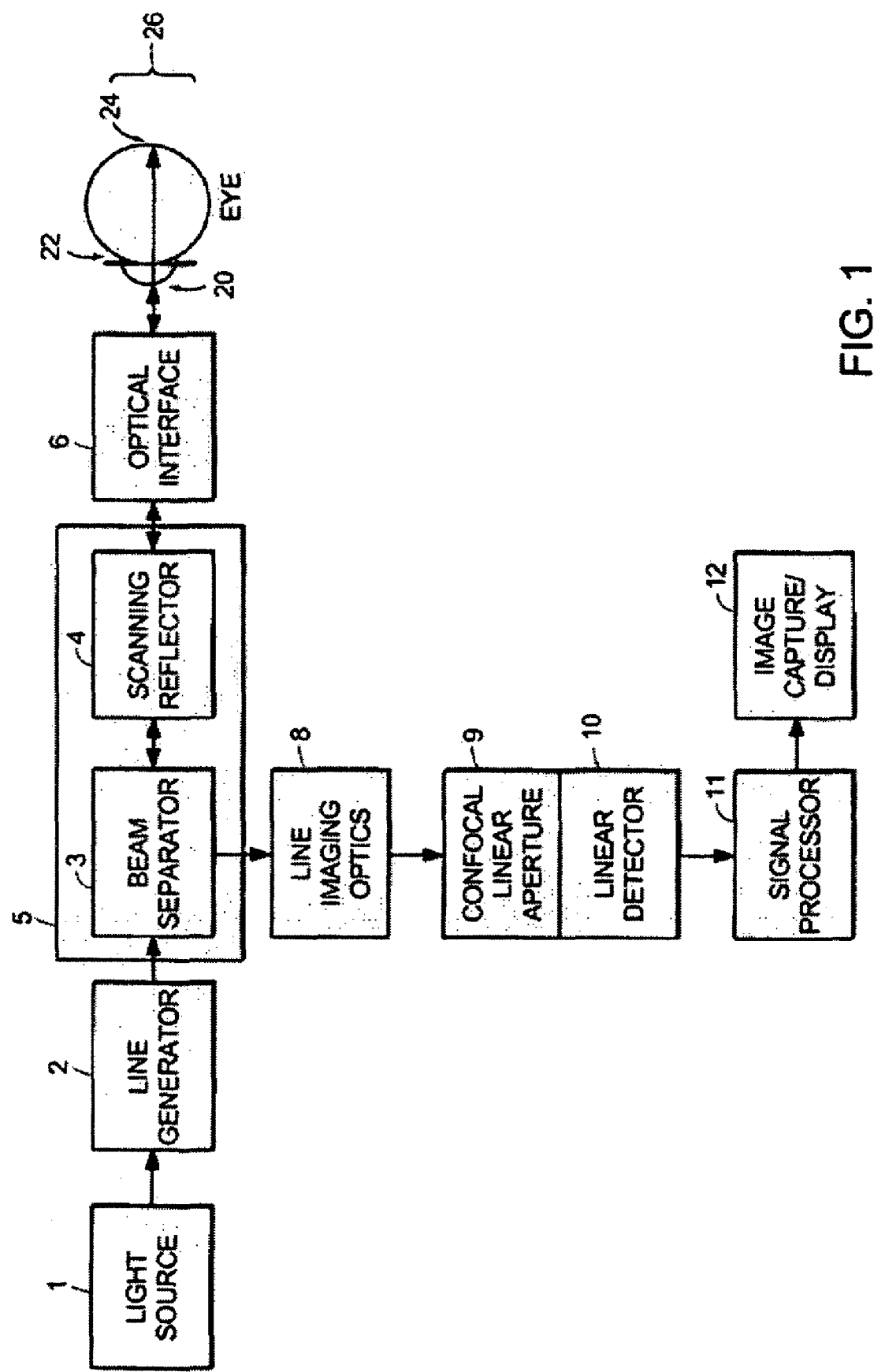
FIG. 1 is a schematic diagram showing an embodiment of a line scanning imaging system, according to principles of the invention.

A line-scanning laser ophthalmoscope (LSLO) of the invention can have significant confocal advantages in image clarity and contrast and depth of penetration at the ocular fundus as compared with conventional digital fundus photography. A hand-held digital LSLO can capture high quality, non-mydriatic (e.g., undilated pupil), line-confocal retinal images; and stereo pairs can be obtained with a simple, compact design with fewer moving parts and components than prior SLO systems. In one embodiment, the system and method can involve a monostatic beam geometry, e.g., the light incoming to the object to be observed and the light collected in reflection from the object pass through the same location in space between the object and the optical component nearest the object. As a result of the monostatic beam geometry, the instrument can be operated with a small, undilated pupil. The instrument remains operative even if the pupil is dilated, however.

There are many benefits that accrue if the pupil of an eye is not required to be dilated. Dilation is generally performed by applying chemicals topically and waiting for the dilation to occur. The waiting period can be on the order of minutes, e.g., twenty minutes. Absence of a dilation requirement means that an instrument embodying principles of the invention can be used immediately, rather than only after a delay necessitated by the dilation of the pupil. This allows use in settings such as emergency or field use, where other instruments become useful only after the dilation of the pupil is complete. Dilation of the pupil causes the patient to have reduced visual acuity for periods of up to hours, until the effect of the dilation chemicals wears off. Dilation of the pupil can require a patient to use protective eyewear or to avoid light of ordinary intensity. Dilation of the pupil can cause a patient discomfort. The use of an instrument embodying principles of the invention can eliminate all of the above negative features of dilation of the pupil.

The inventive technology provides an affordable clinical instrument that gives the clinician the power and resolution of the SLO, with some operational features of the most familiar ophthalmic diagnostic instruments, in an untethered package that is comparable in size and weight to commercial hand-held digital video cameras.

The digital LSLO instrument can be used as a relatively inexpensive multi-mode screening tool to facilitate rapid, non-mydriatic exams for large numbers of patients. In some embodiments of the invention, rapid is to be understood as connoting real time operation. As a portable device, the instrument aids in the early detection of AMD, and other diseases of the elderly, where no economical early warning methods currently exist. The digital LSLO complements existing diagnostics and tele-medicine screening tools for detecting onset of diabetic retinopathy. Many elderly patients can have difficulty in adapting their posture to the demands of any of the standard instruments. Pediatric examination has similar constraints. Instead, instruments should adapt to the needs of the patient. The compact and lightweight LSLO can be used as a hand-held primary care and emergency care aid. The LSLO according to principles of the invention is advantageously used without the necessity to dilate a pupil of an eye, and employs a monostatic beam geometry. At sufficiently low cost, simplified versions of the LSLO can be used by EMTs for head trauma where anomalous bulging of the optic disk is indicative of elevated intracranial pressure, or with blood in the vitreous, as well as for stereo examination of the anterior segment and recording of pupil size and response. High-quality images of injured ocular structures can be captured in a fraction of a second, and transmitted to a treatment center for diagnosis and advice. Veterinary applications include animal certification and identification.

Referring to FIG. 1, an embodiment of a line scanning imaging system is shown in schematic form. FIG. 1 can also be viewed as a schematic diagram showing the steps of a process, such as a method of use of the imaging system, in which each step is represented by a box in the diagram. A light source 1, which in some embodiments is a laser or a superluminescent diode, provides a substantially point source of light. In some embodiments, the light is infrared light. In other embodiments, light within the spectral range from the ultraviolet through the infrared can be provided. The light is received in a line generator 2 and is converted to a line of light. In some embodiments, the line generator 2 is one or more lenses, or a holographic optical element. The line of light from the line generator 2 impinges on a beam conditioner 5 that includes a beam separator 3 and a scanning reflector 4. The line of light interacts with the beam separator 3 and the scanning reflector 4 in either of two sequences. In some embodiments, the line of light interacts with the beam separator 3 before reaching the scanning reflector 4, for example in an embodiment in which the beam separator is a turning mirror or turning prism that intercepts the line of light as it travels in what can be referred to as the incoming direction, e.g., the direction of travel toward the object to be examined or imaged. In other embodiments, the beam separator 3 is a turning mirror or turning prism that receives returning light that has been reflected from the object to be examined or imaged. In either circumstance, the beam separator 3 and the scanning reflector 4 are configured to oblige the incoming light and the returning light to follow separate paths, respectively, between the light source and the beam conditioner 5, and between the beam conditioner 5 and the linear detector 10 (which is further described below). An optical interface 6 such as one or more lenses receives a line of light that scans in a direction perpendicular to the line, and focuses the light on an adjacent object 7 to be examined.

In the embodiment depicted in FIG. 1, the object 7 is a human eye. The eye 7 includes a cornea 20, a pupil 22 and a retina 24. The eye 7 includes a region referred to generally as a fundus 26, which is the interior rear wall of the eye 7. In other embodiments, the object 7 to be examined or imaged is a mammalian eye, or the object 7 is an object of interest that has optical attributes that are subject to examination by a scanned line of light. The incoming line of light is scanned across a portion of the object 7 such as the fundus 26 of the eye. As is well understood, light that impinges an object can be affected in three ways. The light can pass through the object in transmission, the light can be absorbed by the object and can also be re-emitted, and the light can be reflected by the object. For an object of interest such as the eye 7, there can be reflections from some regions of the eye 7, including the front surface of the cornea 20, and the front surface of the fundus 26. Some structures in the eye 7 can absorb and re-emit some of the light, such as layers from the front of the fundus 26 and below the fundus 26. The transmission, absorption/re-emission, and reflection properties of different portions of the object 7 in general can be a function of the wavelength of the incoming light, and can also depend on the structure and composition of the regions of the object 7.

The light that returns to the line-scanning imaging apparatus from the object 7 is a light in the form of a line, which is the reflection and or the absorption and re-emission of the incoming line of light. It is also possible that extraneous light can enter the apparatus, for example as a consequence of operating the apparatus in an environment where ambient light is present. The returning light, which for simplicity can be described as reflected light, is received confocally by the optical interface 6. Depending on the configuration of the beam separator 3 and the scanning reflector 4 in the beam conditioner 5, the returning light is reflected by the scanning reflector 4 in a synchronous manner with the scanning of the incoming line of light, so that the reflected light passes to the line imaging optics 8. The line imaging optics 8 reconfigures the reflected light into a line. The line of reflected light passes a confocal linear aperture 9 and impinges on a linear detector 10. In one embodiment, the beam conditioner 5 is configured to position the beam separator 3 at the conjugate to the cornea 20, and to position the scanning reflector 4 at the conjugate to the pupil 22. In one embodiment, the confocal linear aperture 9 is positioned to be conjugate to the line illumination on the retina 24. The confocal linear aperture 9 can be designed to prevent light that is not confocally received by the apparatus from passing through to the linear detector 10. In one embodiment, the linear detector 10 is a linear CCD array detector, such as a 1×512 pixel linear array. In another embodiment, the linear detector 10 is a 1×N linear CMOS array, where N is an integer greater than 1 representing the number of pixels in the array.

The electrical signals generated within the linear detector 10 pass to an electrical signal processor 11, such as an analog-to-digital (A-to-D) converter that converts analog light levels to digital signals. The signal processor 11 is connected to a processing apparatus such as a commercially available personal computer that can receive, store, and analyze the electrical signals in digital form, for example by use of a frame grabber. The A-to-D and the computer are optionally connected to an image/capture/display module 12, which can include any of a computer monitor or video display, a printer, a plotter, a machine-readable storage medium such as one or more of electronic, magnetic and optical storage media (e.g., memory chips, magnetic disks, CD-ROM, DVD), and an enunciator such as a speaker. In one embodiment, the apparatus is portable, and the linear detector 10 and signal processor 11 apparatus are miniaturized and are provided on one or more semiconductor chips. As is well known in the art, power supplies and motors (which are not shown in FIG. 1) are provided to operate the scanning reflector 4, the light source 1, the linear detector 10, and the signal processor 11. The image capture/display 12 can in some embodiments be a small viewable electronic display, such as is found in a portable television, a cellular telephone, or a personal digital assistant. In some embodiments, the image capture/display 12 is a remote display, for example a display situated in the office of a consulting specialist, who receives the image via a connection such as telephone, television, internet, satellite transmission, or optical fiber interconnection, and who examines the image and provides an opinion thereon.

Different embodiments of apparatus employing principles of the invention include a compact, portable, affordable multi-function LSLO device for confocal visible and NIR imaging, including stereoscopic and dual wavelength operation, and digital image capture and transmission. Such a device is attractive in applications ranging from screening in the elderly to pediatric examination, and from field use or emergency care to veterinary medicine. For example, in field use, high-quality images of injured ocular structures can be captured in a fraction of a second, and transmitted to a treatment center for diagnosis and advice. Veterinary applications include animal certification and identification.

In one embodiment, the line of light is produced by a laser as the light source 1 operated with a fixed cylindrical optic as the line generator 2. The line of light is itself eye-safe for extended periods, even if the scanning reflector 4 were to fail, because, for example, the laser light does not focus to a point in any failure mode. In other words, the apparatus is inherently safer than scanning spot systems. The apparatus presents minimal risk to human subjects without the need for extensive failsafe engineering.

Figure 2A:
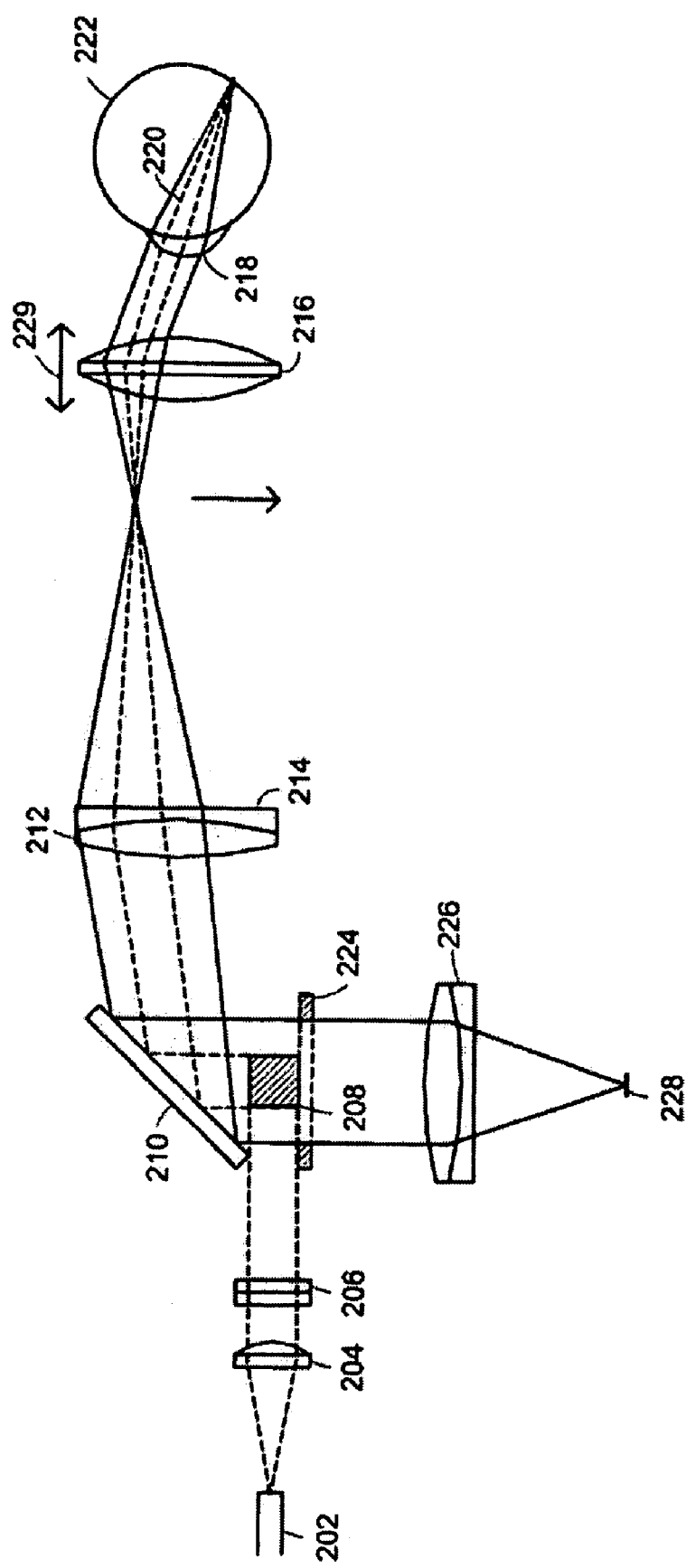
FIG. 2A is a side view of the optical layout of an illustrative line-scanning laser ophthalmoscope that embodies principles of the invention.

FIG. 2A is a side view of the optical layout of an illustrative line-scanning laser ophthalmoscope ("LSLO") that embodies principles of the invention. The LSLO is a simple, compact device which scans a focused laser line on the fundus. A laser 202 provides a substantially point source of light. In the embodiment of FIG. 2A, the light is expanded to a line of light by lenses 204, 206 which are cylindrical lenses. Other optical components can be substituted for the cylindrical lenses 204, 206 to transform he substantially point source of light into a line of light. The line of light impinges on the turning prism or mirror 208, and is redirected to the scanning mirror 210. The scanning mirror 210 is caused to move by a drive, such as a galvanometer motor drive known in the art for driving mirrors. The line of light is scanned by the scanning mirror 210 and passes through one or more lenses 212, 214, 216 which are positioned and/or adjusted to pass the line of light through a cornea 218 of an eye and through an undilated pupil 220 of the eye so as to impinge as a line focused on a fundus 222 of the eye, which includes the retina of the eye.

The reflected light exits the eye through the pupil 220 and the cornea 218, passes through the one or more lenses 216, 214, 212, is redirected by the scanning mirror 210 such that reflected light passes around the turning mirror 208 and passes through the pupil stop 224, reaching and passing through one or more objective lenses 226. The laser line is imaged by the lenses 216, 214, 212, 226 confocally to a linear CCD array 228. In one embodiment, the linear CCD array 228 is a DALSA camera with 512 14 μm pixels. A single galvanometer-driven mirror 210 performs the scan transverse to the laser line. The linear CCD readout is synchronized with scan motion and acquired with a frame grabber. A rectangular image of the fundus is thus obtained.

In one embodiment, the 830 nm laser diode is connected to the optical assembly of the LSLO via an FC fiber cable. 830 nm is an advantageous wavelength to use, because the human eye is insensitive to that wavelength, while infrared detectors having reasonable sensitivity are available. Accordingly, there is little or no pupillary reflex to the light, and little discomfort for the subject of the examination. Other infrared wavelengths can also be used to advantage. By comparison, the human eye reacts strongly to visible light, with both contraction of the pupil and potentially, discomfort and a reaction involving motion of the eye. In the illustrative instrument, commercially available lenses are employed. The digital camera is a commercially available DALSA digital line-scan camera Model CB512, having a linear CCD array 228 (1×512) of 14 μm square silicon pixels. The gain in this model is not fully adjustable. Gain compensation is attained by operation at slower scan rates than are otherwise possible. Different linear CCD arrays 228 with increased gain can be advantageously used.

The DALSA camera body houses a number of low-density circuit cards. The linear CCD array itself is quite compact. A focus adjustment for the laser, and line rotation and displacement adjustments to align the laser line with the linear CCD array are provided with standard Newport tip/tilt mounts, rotary mounts, and slidemounts. The line confocal system is quickly aligned and optimized over the length of the array. The ophthalmoscopic lens slide is used solely to correct for a very large range of ametropia.

In one embodiment, power and computer cables (not shown) attach to the bottom of the DALSA camera body. In a portable embodiment of the LSLO, the connections are eliminated and on-board batteries and an embedded computer are employed. In one embodiment, the device weighs about 3 pounds, and can be lifted and manipulated rather easily.

In one embodiment, the LSLO configuration uses a single-mode fiber coupled 3 mW 830 nm laser 202 with an approximately Gaussian profile. The laser is collimated and passed through a fixed cylindrical optic 204, 206 having 25 mm focal length. The beam remains collimated on one transverse axis, but focuses near the pupil conjugate and then rapidly diverges on the other transverse axis. A 5 mm clear aperture prism mirror 208 turns the beam into the optical train, and also acts as a pupil stop 224 for pupil reflection and some scattered light, according to the Gullstrand principle. The galvanometer driven mirror 210 near this pupil conjugate vertically scans the beam. It has a 14 mm clear aperture. This pupil conjugate is imaged to the eye pupil with the scanning lens 212 (80 mm) and two ophthalmoscope lenses 214, 216, either the Volk Super 66 or the Volk 30 D (66 or 30 diopters), all with NIR anti-reflection coatings. The 830 nm-optimized achromat scanning lens 212 was selected to produce a near diffraction-limited line at the retinal conjugates with good field flatness. These lenses are larger than necessary and are chosen merely for convenience, availability and cost.

The pupil magnification at the turning mirror 208 (a pupil conjugate) with the Volk 66 is 5×, and the beam size at the eye entrance pupil 220 is 1 mm (2.4× magnification and about 2 mm pupil for the Volk 30 D). The measured power at the pupil 220 is less than 2 mW. The eye focuses the beam to near the diffraction limit in the vertical axis on the retina 222, but fans the beam rapidly on the other axis. This reduces the power density at the retina 222, relative to a diffraction-limited spot, by a factor of more than 500, e.g., the aspect ratio of the laser line. For reflected light, the same magnifications give the corresponding size of the scanning mirror aperture at the exit pupil: for the Volk 66, the exit pupil is 3 mm, and for the 30 D, as much as 6 mm. In the latter case, the iris of the eye can be the limiting stop. As long as the pupil is large enough to collect light around the illumination pupil stop, the LSLO functions. The collected de-scanned light is imaged by the objective lens onto the linear CCD array. The lens selected is a 40 mm achromat, but is neither optimized at 830 nm, nor AR-coated. This lens is less critical but can affect in-line resolution to some extent. The use of custom lenses can allow optimization at a selected wavelength.

Figure 2B:
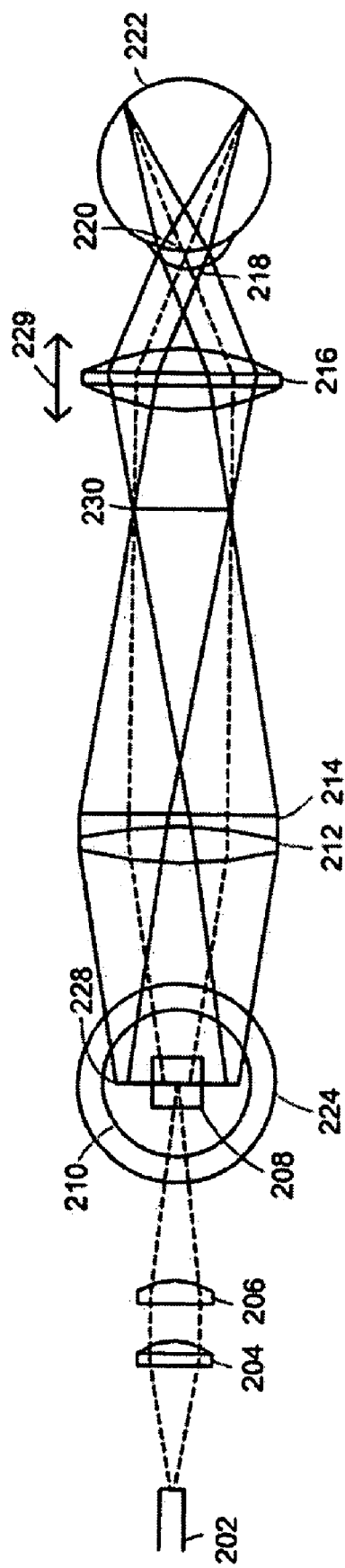
FIG. 2B is a top view of the optical layout of the illustrative line-scanning laser ophthalmoscope that is depicted in FIG. 2A.

FIG. 2B is a top view of the optical layout of the illustrative line-scanning laser ophthalmoscope that is depicted in FIG. 2A. Both the top and side view are shown because the cylindrical optic 204, 206 requires both tangential and sagittal views to visualize its operation. The side view shows the pupil separation at the small turning prism mirror 208 that allows the illuminating (incoming) beam to pass to the retina 222 while acting as a stop for corneal reflections. In this view, the LSLO is indistinguishable from its point-scanning cousin, the SLO. The top view shows the action of the cylindrical lens 204, 206 which focuses at the pupil conjugate and diverges to a tightly focused laser line 230 at the retina 222. The line 230 is scanned on the retina 222 by the scanning mirror 210 and the reflection is descanned and imaged to the linear CCD array 228. The LSLO of the present invention preserves advantages such as rejection of interfering scattered light, and rejection of light scattered from defocused planes above and below the focal plane, even though an entire line is imaged at once.

Both transverse and longitudinal characteristics of the imaging systems of the invention can be considered in describing the theoretical performance limits of the systems. Diffraction at the focal plane, and scattered light reflected from other defocused planes are analyzed. The purely focal plane case, as with a planar target such as a resolution chart, is to be distinguished from volume targets such as biological tissues that reflect light from multiple planes. In the following, "focal plane" is understood to mean a conjugate to the image plane where the detector or confocal aperture lies.

Figure 3:
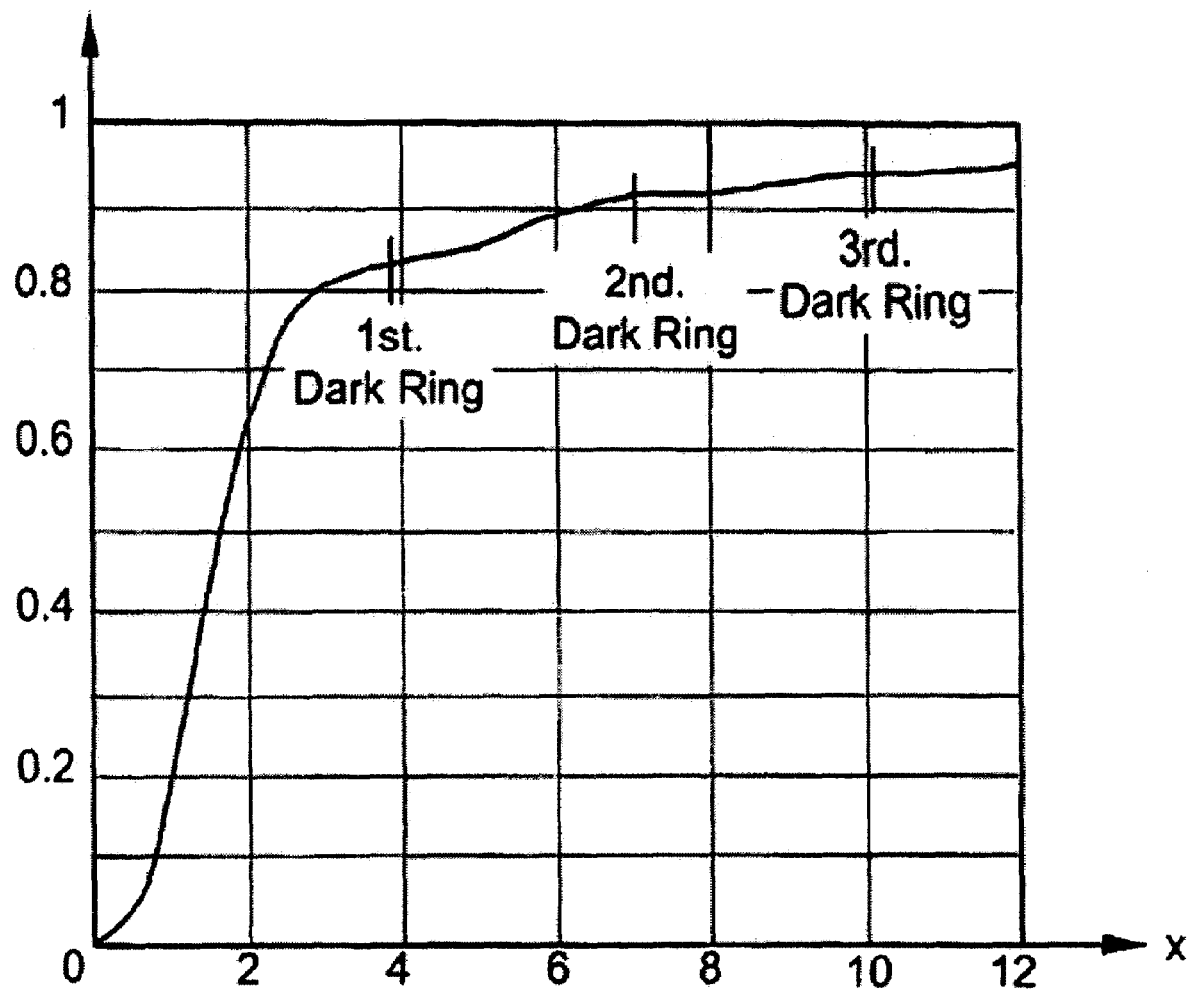
FIG. 3 is a diagram showing the integrated power falling within a circle of a given radius, according to the prior art.

One characteristic of an imaging system is its Modulation Transfer Function (MTF) or equivalently its Point Spread Function (PSF). These functions describe how the image of a point source is broadened in the image plane. In a diffraction limited system imaging diffuse reflections, the PSF is the familiar Airy pattern for reflected light emerging from the target and filling the collection aperture. The integrated power falling within a circle of a given radius is shown in FIG. 3, which is well known in the prior art. In the focal plane case, one can think of the interfering light as contributions from the wings of the total PSFs, including aberrations, of adjacent illuminated regions. The farther away these imaged points are from a particular confocal aperture (or pixel), the weaker their contribution to the background light. The total power at any given pixel is the sum of all such contributions over the entire illuminated area (ignoring scattering). When used to probe a cavity such as the eye, the SLO is ideal and nearly background-free because there are no other illuminated regions: the "flying spot" is the only light source. The total LSLO background pixel power is effectively a line integral along a strip through the center of the PSF since only a line of illumination is used. As a result of the linear scan, there are contributions from the left and right of each pixel, but the regions above and below the line are dark. Ordinary CCD imaging however, is a complete surface integral over the PSF, to the limits of the illuminated area. The limiting contrast is found from FIG. 3 by reading the percentage of total energy at the central pixel's edge, whatever its size may be. The focal image contrast is best for the SLO, and worst for standard fundus imaging. The LSLO lies somewhere in between. The sharper the PSF relative to the pixel size, the smaller the difference in focal plane performance of the LSLO relative to that of the SLO.

The contribution of out-of-focus regions above and below the plane of focus need to be considered for the case of a volume scattering medium. A significant performance enhancement can be realized with confocal imaging. Three imaging schemes are illustrated in FIGS. 4A-4C.

Figure 4A:
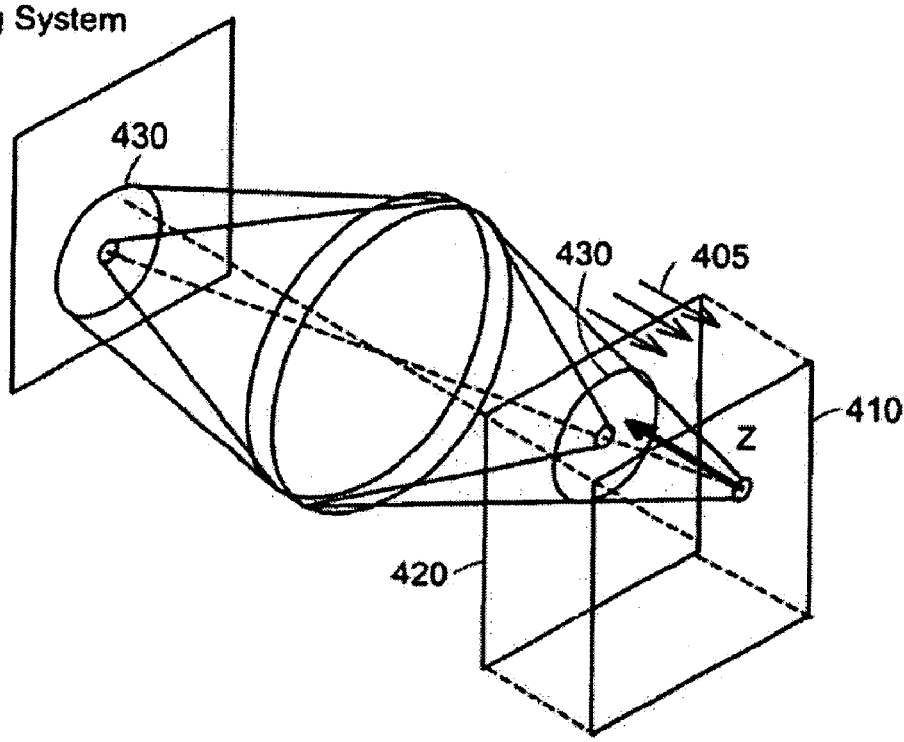
FIG. 4A illustrates the optical effect of defocusing in a prior art full field imaging method.
Figure 4B:
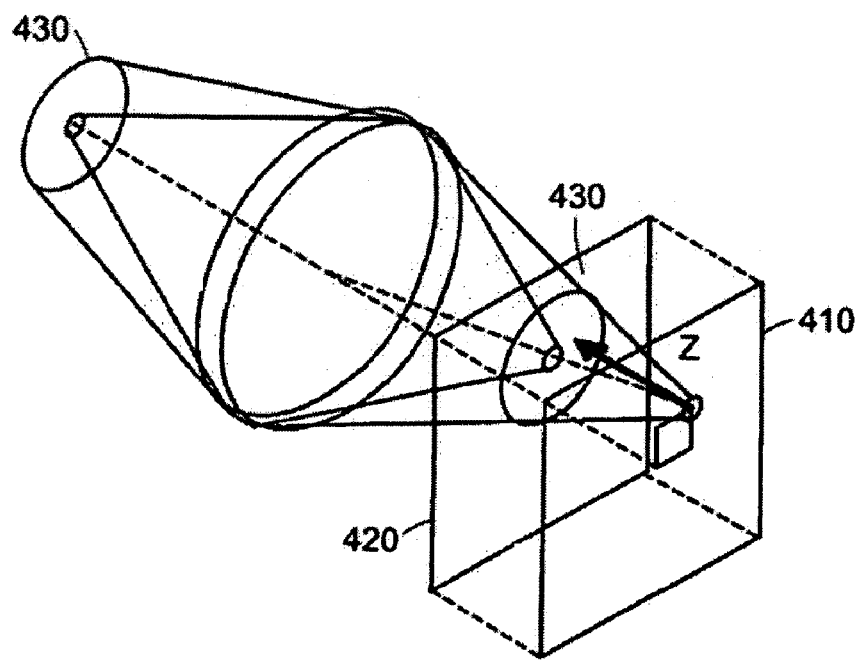
FIG. 4B shows the optical effect of defocusing in a confocal "flying spot" system of the prior art.
Figure 4C:
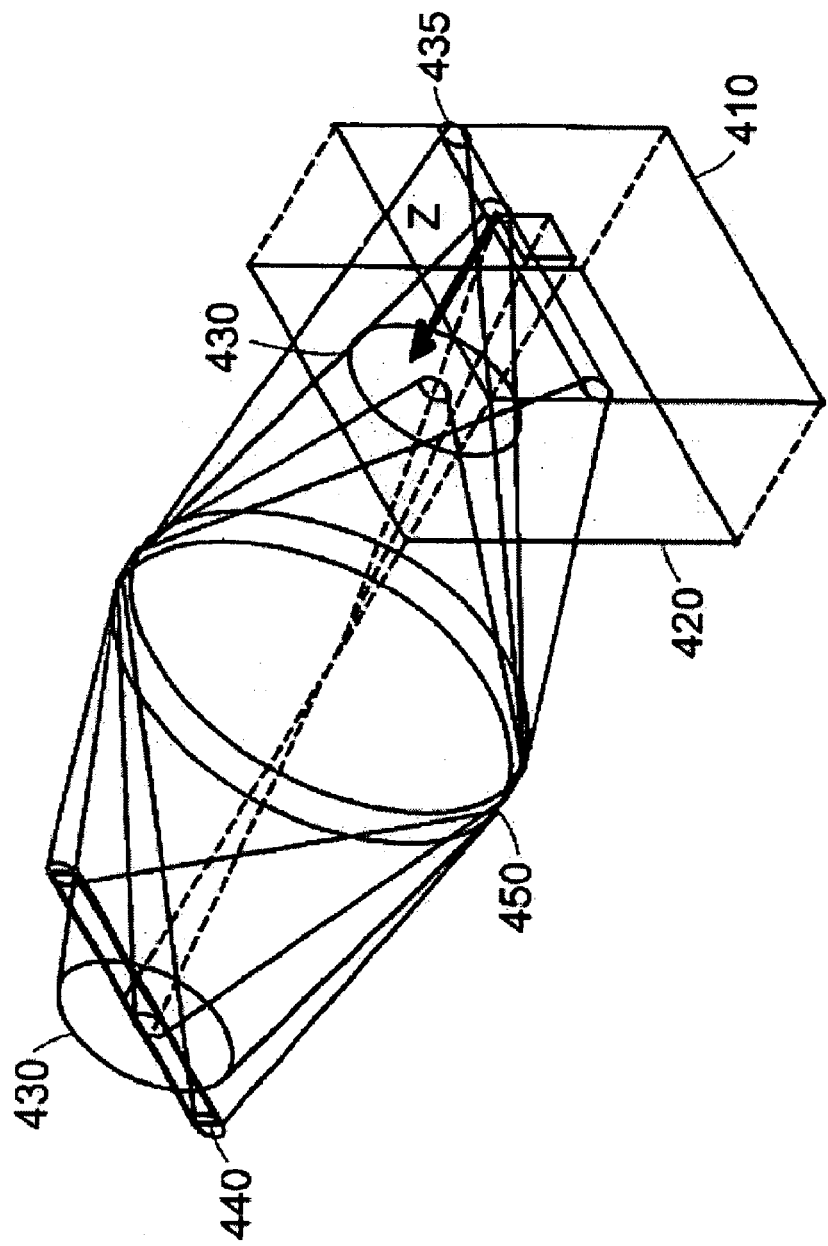
FIG. 4C illustrates the optical effect of defocusing in a line scanning imaging system such as the LSLO of the invention.

FIG. 4A illustrates the optical effect of defocusing in a prior art full field imaging method. When the media above or below the focal plane scatters light, the use of full field illumination results in a severe defect. In FIG. 4A, uniform light 405 impinges on a focal plane 410. A reflection at a defocused plane 420 at distance Z from the focal plane 410 can provide a defocused image 430 comprising a large blur circle at the detector plane. The behavior of the intensity with Z is analyzed for three cases, namely full field imaging, "flying spot" imaging, and line scan imagining.

From optical theory, for unit magnification over Area A with uniform illumination $I_o$, where the reflectivity function per unit volume of media is $\Delta(X,Y,Z)$, and the imaging system f-number is F, the total reflected light intensity at the image plane I (X,Y) is given by Equation (1):

$$I(X,Y) \propto \int_Z \int_{A(Z)} \frac{I_o \rho(X,Y,Z) dA dZ}{\left[\left(\frac{Z}{2F}\right)^2 + (\lambda F)^2\right]} \quad (1)$$

The function of Z, obtained by first integrating over the area at each Z plane, is a "range gate" which describes sensitivity to scatter from regions above or below the focal plane. Actual evaluation of these integrals is made rather complex by aperture shape. However, the approximate dependence of the area integrals on Z can be found by inspection. The intensity of the defocused reflected light at each pixel drops off as $Z^{-2}$. The area producing this illumination on that pixel increases with $Z^2$. This occurs at every layer in the sample. Integrating just over area, the resulting range gate function is approximately constant, i.e., independent of Z. This means there is no effective range gate. Every layer in the resulting image is weighted only by it intrinsic reflectivity. Unless the reflectance is strongly confined to a region very near the focal plane, the image contrast is quickly overwhelmed by defocused light.

The MTF can written as a function of spatial frequency (k) as given in Equation (2):

$$MTF = \frac{[I_{max}(k) - I_{min}(k)]}{[I_{max}(k) + I_{min}(k) + 2I_{defocus}]} \quad (2)$$

where $I_{min}(k)$ and $I_{max}(k)$ give the ideal focal plane contrast at given spatial frequency, and the defocused light intensity shows the effect of background light on contrast: $I_{defocus}$ increases directly with Z-thickness in a uniformly scattering medium. Therefore, the full field imaging method is unsuitable in scattering media where the thickness of the sample is greater than the depth of field scale ($8F^2$). Contrast is halved when volume-integrated scattering anywhere in the optical path is equal to the focal plane reflection. This is the source of the sensitivity of conventional fundus image contrast to media clarity.

FIG. 4B shows the optical effect of defocusing in a confocal "flying spot" system of the prior art. The equation for the intensity I(X,Y) remains the same except for a modification as a consequence of focusing the illuminating laser light to a point confocal with the aperture. This adds an identical defocus factor in the denominator in Equation (1). The range defocus light falls off as $Z^{-4}$, rather than $Z^{-2}$. Integrating over area, the resultant range gate function has dimensions of $Z^{-2}$. The full gate width at half maximum is just the usual definition of the depth of field. This weighting of Δ is integrable in Z, so that uniform scattering from surrounding tissue does not destroy focal plane image contrast. The confocal flying spot method of the prior art provides intrinsic sectioning properties, limited only by extinction due to absorption and scatter.

FIG. 4C illustrates the optical effect of defocusing in a line scanning imaging system such as the LSLO of the invention. For a line scanning system, the system focuses the laser light 435 to a line confocal with the linear detector array 440 by use of optical components 450. In this configuration, the illumination intensity falls off as $Z^{-1}$. The defocused intensity therefore falls off as $Z^{-3}$. Integrating over area, the resultant range gate function has $Z^{-1}$ dependence, with a gate width proportional to the depth of field. However, this weighting of Δ is not integrable in Z. Rather, it has only a weak logarithmic divergence. Uniform scattering from surrounding tissue can reduce focal plane image contrast. Nevertheless, a line scanning system provides useful sectioning properties, because contrast falls off much less rapidly in thick samples, and is far less sensitive to more remote media opacities.

Laser imaging systems generally tend to exhibit speckle patterns, and this is so for both the SLO and the LSLO. Except near smooth interfaces with changes in refractive index, biological systems tend to scatter light from spatially distributed sites, with sizes and separations from nanometers to microns. Because the laser light is spatially coherent, this means that the phase relationships of the reflections along the beam (at least within one coherence length) are preserved. The total intensity of the light collected from such a region is the coherent sum of many contributions. The random walk nature of the amplitude sum leads to constructive and destructive interference with large variations in power falling on the aperture or on each pixel, especially if the aperture or the pixel size is near the diffraction limit. The diffraction limit can be thought of as "one speckle" in the transverse direction. This effect is frequently countered by using a less confocal (larger) aperture collecting light over a larger area which tends to average away some speckle. This solution is not available for the LSLO, and LSLO imaging is roughly equivalent to so-called "tightly confocal" SLO imaging. The effective image resolution is roughly halved in the coherent case.

A significant improvement is realized by using super-luminescent diode illumination. Current commercial devices with 25 nm bandwidth and about 10 μm coherence length are available at low prices, with power levels of a few milliwatts. Over the depth of field in the tissue, the speckle can substantially average away, producing smoother less granular images without loss of transverse resolution.

The light gathering behavior of a LSLO embodying principles of the invention is compared to a standard point-scanning system. The model used for calculation assumes identical optical geometries and detector quantum efficiencies. Both systems are modeled to scan vertically at the framing rate. For a 500×500 image at 30 Hz framing rate, the horizontal scan rate $f_H$, of the SLO is 15 kHz. The "flying spot" detector requires a bandwidth of $f_H$ times the number of pixels per line, $N_{Hpix}$. To resolve 500 horizontal pixels at 15 kHz, the bandwidth is more than 10 MHz. This can be achieved because the full power of up to a few milliwatts is focused at the retina confocally with the detector aperture. The reflected power collected depends upon the incident power $P_I$ (say 1 mW), the local reflectance, R(X,Y), of the retina (less than 10% in NIR), and the collection solid angle Ω (about $10^{-3}$ sr). This amounts to a typical range from about 1 to about 100 nW. The noise-equivalent power (NEP) of the silicon detector is one noise contribution, and another is shot noise. An acceptable signal-to-noise ratio SNR is easily reached within the required bandwidth. The dynamic range of 8-bit images requires a SNR>255 to fully utilize the available range, that is, a noise level less than the signal strength represented by the least significant bit.

For this case the SNR can be written as:

$$SNR = \frac{[\eta R(X,Y)\Omega P_1]^2}{NEP(f_H N_{Hpix}) + (\eta R \Omega P_1 E_v f_H N_{Hpix})} \quad (3)$$

where η is the quantum efficiency and $E_v$ is the energy per photon at the illuminating wavelength. The thermal noise of a small silicon photodetector can be about $10^{15}$ W/(Hz)$^{1/2}$. Readout noise of a read-out amplifier can dominate the NEP for silicon photodetectors. Depending upon collected power, the SNR can be limited by either detector/amplifier noise or shot noise. When dominated by shot noise the SNR becomes:

$$SNR = \frac{\eta R \Omega P_1}{E_v f_H N_{Hpix}} \quad (4)$$

The LSLO images an entire line at once. No transverse scan is required. The readout of the linear CCD array represents a "scan," but it can be performed during the time that the line is repositioned. The effective integration time is $1/f_H$, instead of $1/f_H N_{Hpix}$ as for the flying spot system. For the same average power at the retina, the line scanner must spread the beam with a cylindrical optic to form a line covering all $N_{Hpix}$ at once. In other words, the power at each pixel is reduced in proportion to the number of pixels: $P_I$ per pixel for the SLO becomes $P_I/N_{Hpix}$ for the LSLO. Therefore the equation, and the shot-noise limited SNR, is unchanged and the line scan and flying spot systems are equivalent as regards SNR. However, because the instantaneous power per pixel is smaller by $N_{Hpix}$ for the LSLO, while the detector/amplifier NEP term only drops by $(N_{Hpix})^{1/2}$, the detector/amplifier thermal noise contribution is $(N_{Hpix})^{1/2}$ times greater. High quality linear CCD arrays/amplifiers are able to operate near the shot noise level of a few hundred photoelectrons before other noise sources become important. Excessive noise can appear as snow over the acquired images, even over and above the speckle noise. No such noise has been observed at the quoted eye-safe light levels.

The model can also be extended to evaluate the full image case of the prior art. For a square CCD array in full field operation, the power level per pixel is reduced still further by another factor of $N_{lines}$ (approximately $N_{Hpix}$). The detector/amplifier noise is most likely to dominate, and CCD imaging becomes noisy at these low eye-safe light levels. Flash fundus imaging or higher illumination powers must be used, and all confocal advantages are lost.

The operation of the LSLO has been tested to determine the resolving power and diffraction limits of the system, using both biological samples, such as an eye, and inanimate, mechanically produced targets.

The width, w, of the laser line beam at the retina, (to the first null in the Line Spread Function) is given by:

$w/2n8f_{eye}/d \sim 38$ microns with the Volk 66, or ~19 microns with the 30 D, for the eye, and $w/28f_{model}/d \sim 42$ microns with the Volk 66, or 21 microns with the 30 D, for the model eye.

In one embodiment, the best focused beam width based on resolution targets appears to be somewhat larger. This is attributable in part to aberrations in some non-optimized elements with the optical train, and perhaps to forward scatter from optical surfaces. The pixel size referenced to the retina is designed to roughly match these beam widths. For the Volk 66 and 30 D, the pixel diagonals at the model retina are 40 μm and 20 μm, respectively. The horizontal and vertical Nyquist limit is twice the pixel spacing or 56 μm and 28 μm for the two magnifications, or 17 and 35 line pairs per millimeter.

With a fixed 3 mm eye entrance pupil, or about 7 mm and 14 mm at the pupil conjugate for the Volk 66 and 30 D respectively, the Airy diffraction at the CCD array due to the 40 mm objective is 11.7 μm and 5.8 μm. To first approximation, the net double-pass image optical resolution element is the root-mean-square sum of these contributions, or 58 μm and 29 μm. This closely matches the Nyquist limit of the pixel array.

Figure 5A:
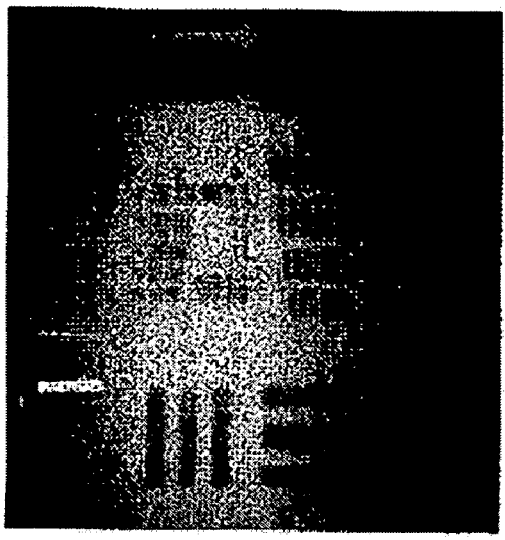
FIGS. 5A and 5B show the standard prior art United States Air Force (USAF) resolution target #51 at low and high magnification, respectively.
Figure 5B:
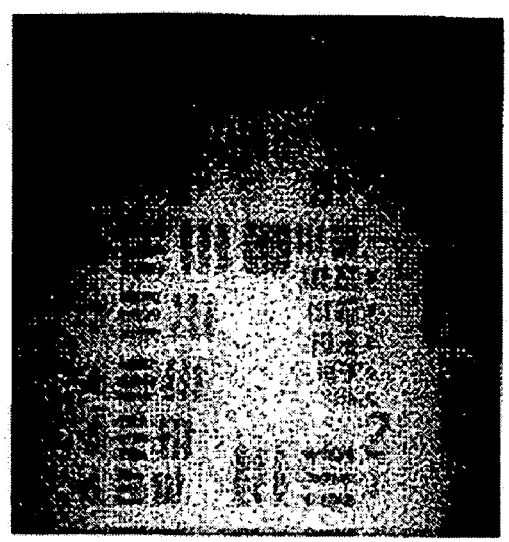

FIGS. 5A and 5B show the standard United States Air Force (USAF) resolution target #51 at low and high magnification, respectively. Because the model eye consists of an achromat in front of the planar target, ophthalmoscopic lenses overcorrect for field curvature that can be present in the eye. The bright central region is due to field curvature moving target plane out of the depth of field at high scan angles. Resolution is determined by reading off the group and line number of the smallest resolvable line triplet. Despite some focus irregularities of the Volk 66 lens interacting with the model eye optics, the resolutions, judging from the limits of visibility of the USAF target triplets, are:

For low magnification 40 degree field: group 2, line 6, corresponding to 7 line pairs per mm or 143 μm per line pair For high magnification 20 degree field: group 3, line 6, corresponding to 14.3 line pairs per mm or 70 μm per line pair.

Figure 6A:
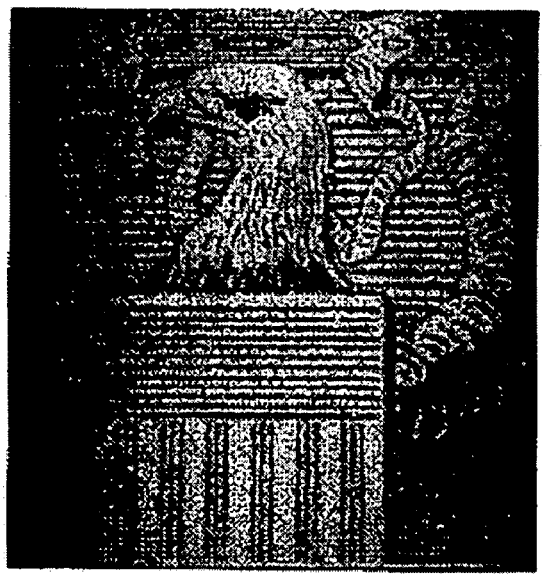
FIGS. 6A and 6B show prior art target images that appear on the reverse of a United States one dollar bill.
Figure 6B:
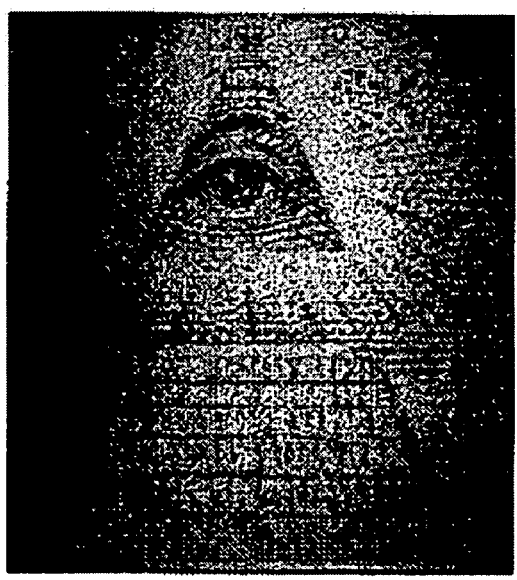

In each case approximately 5 pixels can be counted between lines at the limiting resolution. These resolution values are approximately twice the calculated incoherent values, as expected. The contrast is expected to vanish near the Nyquist limit, and the threshold of visibility for coherent illumination can lie somewhat above this limit, e.g., by a factor of two. The slight translucence of the matte target surface itself gave rise to apparent reduction of the contrast having nothing to do with LSLO optics, as well as a highly speckled appearance, which has an adverse impact on apparent resolution. Denser targets (e.g. images that appear on the reverse of a United States one dollar bill) placed directly at the first retinal conjugate (no Volk lens) have an improved appearance as in FIGS. 6A and 6B. Another interesting effect observed is the difference in contrast between the horizontal and vertical bars, seen clearly in FIG. 5B. This can be understood as the effect of the proximity of bright pixels to the left and right on the imaged line. The vertical bars, being only two or three pixels wide have considerable background contributions from the neighboring bright regions, whose PSF extends over two pixels. However, on the horizontal dark lines, adjacent pixels on the line are dark except at the ends of the lines, with little or no consequences for contrast.

The widths of the laser line were w/2n8f/d~40 microns with the Volk 66, or ~20 microns with the 30 D. The length of the laser line was set to cover the fields of interest of about 40 degree and 20 degree horizontal. In order to have minimal variations in brightness along the 7 mm CCD array, the FWHM has been scaled via the focal length of the fixed cylindrical lens, to no less than 7 mm at the model retina. Approximately 1 mW of power falls fairly uniformly on the central 7 mm of the line, which is useful for power density calculations in the worst case (e.g., use of the 30 D optic):

Length, L~0.7 cm.

Stationary Line Power Density at the retina 1 mW/(wL) ~500 mW/cm$^2$. Safe exposure times at such power densities at 830 nm is at least 10 seconds, and consistent with the time needed to for the subjects to avert their gaze, or for the operator to block the incoming light or turn off the light source in the event of scanner failure.

A plane wave equivalent at the cornea can be estimated by determining the power at the cornea which corresponds to this power density on a single 30×30 micron spot, i.e., one virtual laser element of the line. This is simply {fraction (1/250)}$^{th}$ of the incident power, or less than about 4 μW.

When scanned vertically through 0.7 cm to form a square image, the time average power density at the retina drops further to less than {fraction (1/300)}$^{th}$ of this power: Average Power Density of laser line scan (full field 7 mm×7 mm)~2 mW/cm$^2$.

The key safety feature of the LSLO is that even if the vertical scanner fails, no laser interlock is needed because the stationary line itself is eye-safe over the few seconds required to move the volunteer's eye away. The fixed cylindrical optic, which cannot be removed without disassembling the instrument, ensures that the power density at the retina is lower than the quoted values.

The LSLO of the invention has been compared with SLOs of the prior art through the acquisition of wide field images. Forty degree field LSLO images in the left and right eyes of a human subject are shown in FIG. 7. Sharp images were obtained with the LSLO, and typical characteristics of confocal infrared image were seen: a dark disc, well-resolved bright vessel lumen, lighter arteries and darker veins, foveal reflex in some subjects, capillaries and choroidal vessels, and variations in pigmentation. The left eye above shows a retinal scar and some residual features of prior central serous retinopathy. Because of the relatively small pupil required for these images and the modest depth of field, clear images can be obtained well into the periphery. For comparison, a standard SLO image of the prior art at slightly higher magnification is shown in FIG. 8.

Figure 9A:
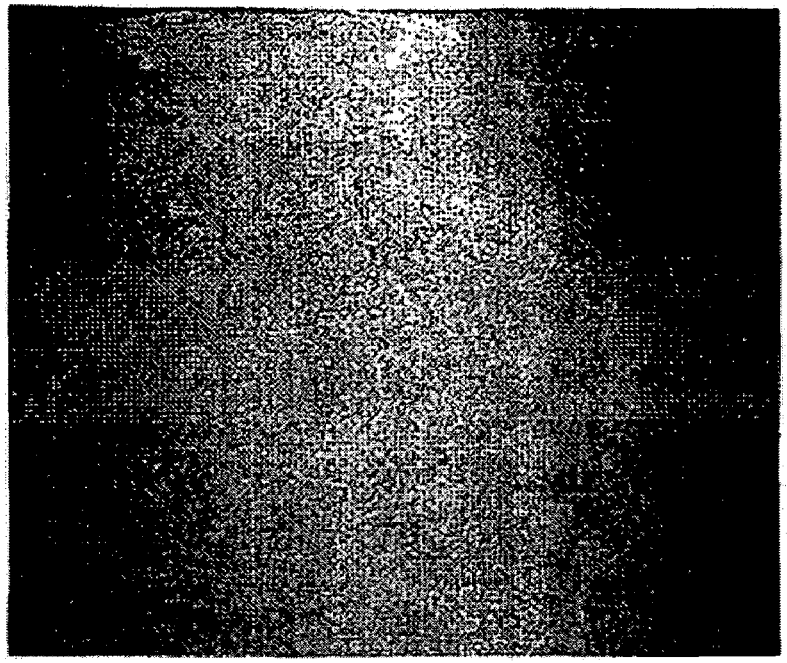
FIG. 9 shows twenty degree field LSLO images in a human subject, according to principles of the invention.
Figure 9B:

The capabilities of the LSLO of the invention are demonstrated by recording macular and disc images. A selection of twenty degree field LSLO images in a human subject are shown in FIG. 9. The images distinctly show veins and arteries, retinal nerve fiber foveal reflex, and other morphology.

In some embodiments, the LSLO provides the ability to collect stereo pairs. In conventional stereo imaging, the pupil aperture is optically split and two images are captured corresponding to the left and right fields. The parallax between the images contains the depth information. Depth of field is determined by the numerical apertures of the individual fields. Because of the finite depth of field of the LSLO with different viewing angles, it is equally effective at gathering depth information. But in addition, due to its confocality, defocused light from above and below the plane of focus is suppressed. This allows superior 3D visualization of deeper retinal structures.

Figures 10A, 10B:
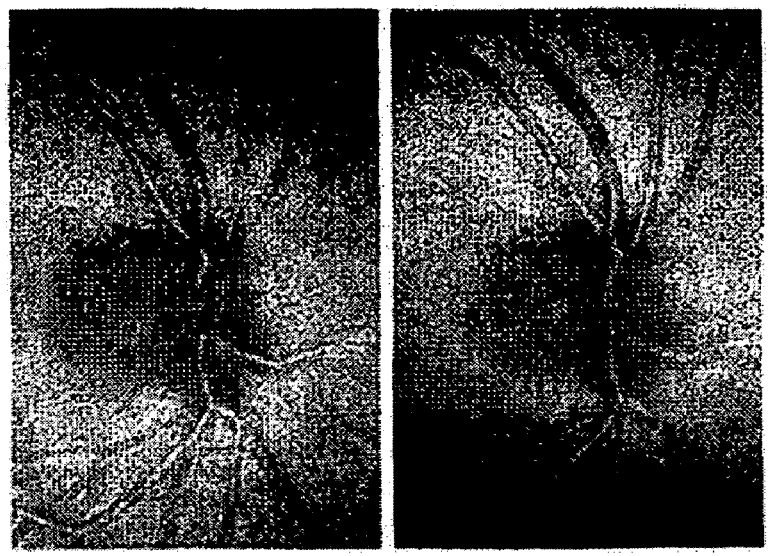
FIG. 10 shows illustrative disc image pairs captured in succession with the LSLO, according to principles of the invention.

FIG. 10 shows illustrative disc image pairs captured in succession with the LSLO, with an approximately 1 to 2 mm lateral shift in pupil position. This purely lateral pupil shift allowed the same image to be captured at two viewing angles separated by 3 to 6 degrees and is an effective simulation of anticipated live-motion, split-pupil aperture binocular LSLO operation. These images are displayed side-by-side in FIG. 10 at the appropriate separation, so that when viewed from 2 feet (60 cm) or more from the page, the image can be made to fuse in a stereo view.

In FIG. 10, the shapes and orientations of the vessels near the disc are clearly visible. Left/right focus is slightly different due to successive image capture. The perception of a mild fogginess in the images is due to the low resolution in the images (500×512), and speckle. High resolution images, and perhaps super luminescent diode (SLD) illumination, can reduce granularity.

Figure 11:
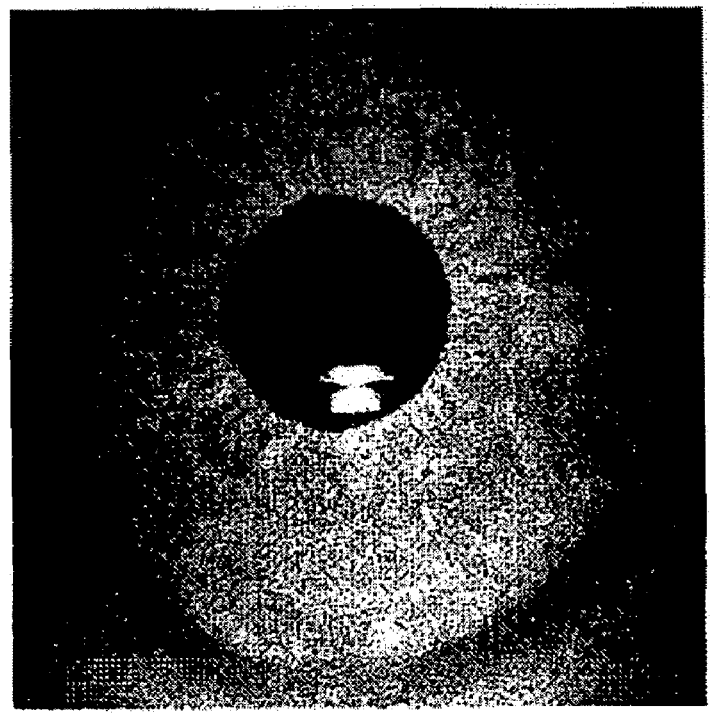
FIG. 11 is an image that illustrates confocal and anterior segment imaging, according to principles of the invention.

FIG. 11 shows a demonstration of confocal and anterior segment imaging. The image of FIG. 11 was obtained when the ophthalmoscopic objective was removed and the anterior segment of the subject's eye was placed at the conjugate image plane.

An embodiment of the LSLO of the invention preferably operates at two magnifications, and is configurable to permit imaging of an anterior segment and non-mydriatic imaging of the posterior segment. In one embodiment, this is accomplished using one of two interchangeable ophthalmoscopic lenses with rotary focus. In other embodiments, the ophthalmoscopic lenses are demountable, and can be interchanged, or the LSLO can be operated without an ophthalmoscopic lens. The LSLO device incorporates all necessary electronics and optics for image acquisition, without the need for external image acquisition, a computer or a CRT. The LSLO device provides on-board camera captured image storage and image downloading.

In some embodiments, the use of two substantially similar instruments together can provide additional functionality. Dual channels can be integrated that can be configured for multi-wavelength operation and real time binocular imaging. Wearable micro-display technology permits the operator to manipulate the device with an unobstructed visual field, while glancing a few degrees off axis, such as upward or downward, to the color/stereo (left and right eye) display. The displays appear to merge near the hand-held device so that minimal accommodation is needed while shifting gaze from patient to stereo display. The use of an adjustable facial support system or mask, which makes possible the operator gently holding the apparatus in place adjacent to the patient, provides all the stability and articulation that the lightweight LSLO needs for patients in any orientation.

In one embodiment, the a LSLO can be used to monitor blood flow in the retina. The LSLO can be combined with a retinal tracking device. For example, a TSLO can serve as the platform for SDF blood flow measurements. Suitable retinal tracking devices include the servo tracking systems described in U.S. Pat. No. 5,767,941 and U.S. Pat. No. 5,943,115, both of which are owned by the assignee of the instant application and the disclosures of which are incorporated herein by reference in their entireties. In one embodiment, the retinal tracking device tracks at a rate that exceeds the maximum rate of motion of an eye (e.g, with a bandwidth greater than 1 kHz). The retinal tracking device can improve the resolution of the LSLO.

Figure 12:
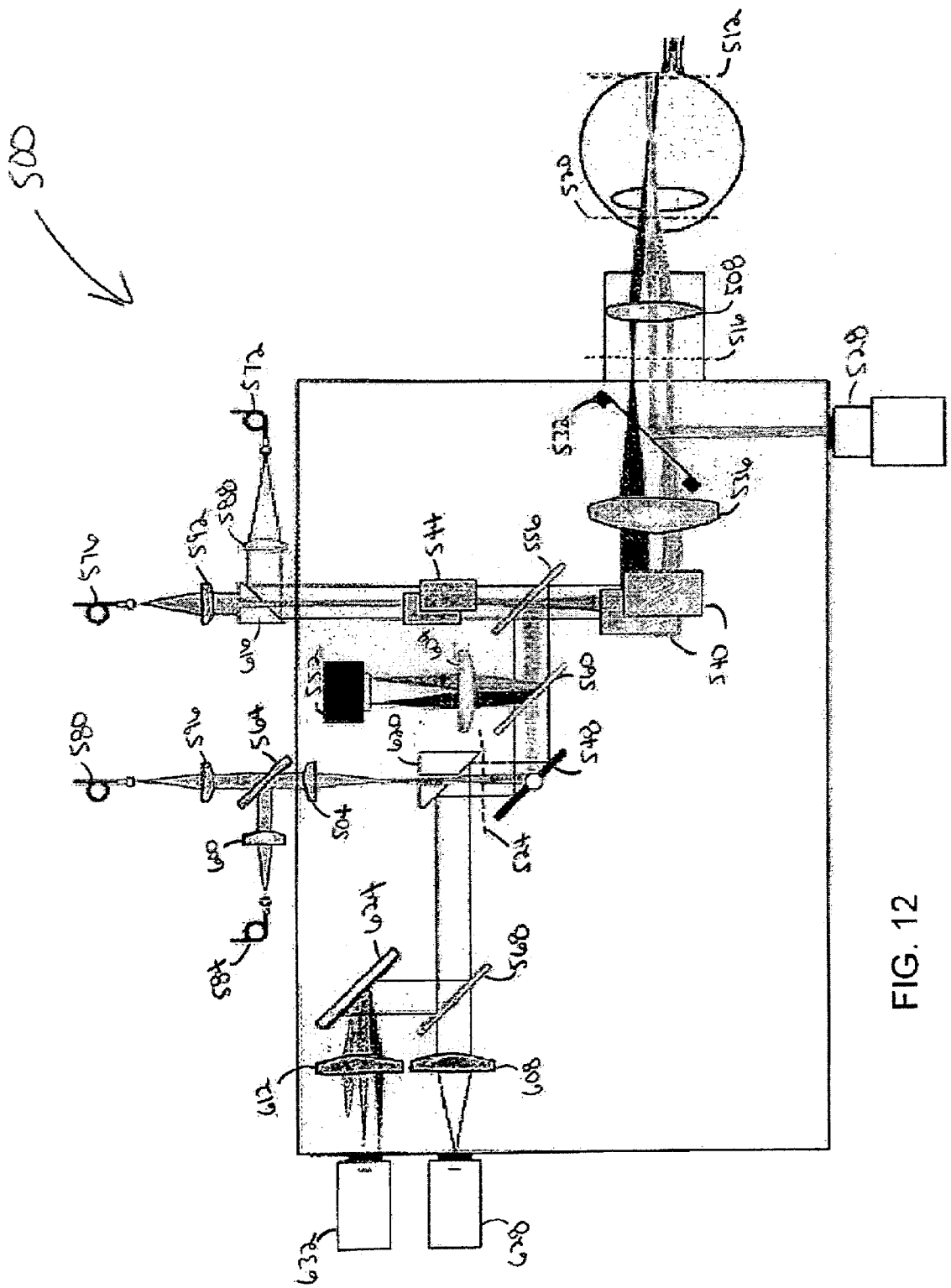
FIG. 12 depicts an optical layout for an exemplary TSLO according to the invention.

The optical layout for an exemplary TSLO 500 is shown in FIG. 12. The view is from the side of the instrument, although some modules are perpendicular to that shown in FIG. 12. Beams depicted by solid rays are incident upon the retina, and beams depicted by open rays are reflected light from the retina. The beam after cylindrical lens 504 is focused in only one axis. The other elements include ophthalmoscopic lens 508; retinal plane 512; retinal conjugate 516; pupil plane 520; pupil conjugate 524; fixation target 528; pellicle beam splitter 532; f/2 scan lens 536; tracking galvanometers 540; dither scanners 544; image galvanometer 548; stimulus source 552; long-pass dichroic beam splitters 556, 560, 564, 568; fibers 572, 576, 580, 584; f/2 lenses 588, 592; f/3 lenses 596, 600, f/2 lenses 604, 608, 612; beam separators 616, 620; and grating 624.

The white-light fixation target 528 that was part of the slit lamp biomicroscope was incorporated into the TSLO 500 with a pellicle beam splitter 532. The achromatic 76.2-mm focal length (fl) scan lens 536 images light from the retinal conjugate 516 to the detector arrays 628, 632. The position of the scan lens 536 is offset from the image illumination and detection optical axis to reduce backreflections from the lens. The primary illumination source 580 is a single-mode fiber-coupled, 2.5-mW, 780-nm, laser diode (Thorlabs, Inc.). A second visible or near-infrared illumination source 584 can also be used with the additional fiber port and dichroic beam splitter 564. The illumination source is collimated with a 38.1-mm fl lens 596, 600 and focused in one axis with a 12.7-mm fl cylindrical lens 504. The cylindrical lens is used to fan out light rays in one dimension while rays in the orthogonal dimension remain collimated. Therefore, the retina can be illuminated with a single line and only a single scanner is required for imaging. The illumination line width on the retina (11-µm with the Volk 66 D opthalmoscopic lens) is determined by source fiber size (5.5-µm mode field diameter) and optical magnification, subject to the limits of diffraction and aberrations.

The illumination beam is scanned with a galvanometer-driven mirror 548 (Cambridge Technology, Inc.). The image galvanometer 548 simultaneously scans the illumination beam and descans the reflected light from the fundus. Quasi-confocal images are created absent of reflections from the cornea by placement of a separator 620 and the image galvanometer 548 near the secondary pupil plane. The image entrance and exit pupils, determined by separator 620, are ~4 and 13 mm, respectively. The backscattered near-infrared light is imaged onto a digital line-array detector 628 (Dalsa, Inc.). For image synchronization purposes, the scanner is master and the line array detector is slave. The detector pixel size (14 µm×14 µm) acts as the confocal aperture in one dimension. Since a cylindrical lens and line-array detector can be used, the image-detection scheme can be considered quasi-confocal.

Scattered light from adjacent spatial voxels are collected in the transverse direction parallel to the scan and rejected in the orthogonal direction. Because a CCD can be used rather than a photomultiplier tube or an avalanche photodiode (APD), the detector response is lower than that for a conventional research SLO. Thus, the 780-nm illumination beam power measured at the cornea was between 0.5 and 1 mW. However, since the light at the retina is entirely spread out in one transverse dimension even with the image scanner off, the radiant exposure (in joules per square centimeters) is well within maximum permissible exposure safety limits. Although disadvantages of this optical arrangement are decreased signal-to-noise ratio, correspondingly higher illumination beam power required, and a lower degree of confocality, the system requires one fewer scanner and is considerably more compact than a conventional confocal SLO.

A monochromator module (which can include dichroic beam splitter 568, grating 624, and lens 612) can be incorporated into the optical path to detect multiple visible and near-infrared wavelengths. The dual-wavelength illumination-detection module can be used for fluorescent and hyperspectral imaging applications, for example, to target and quantify macular pigment and photopigment or subretinal structures. A stimulus module (which can include dichroic beam splitter 560, lens 604, and stimulus source 552) can be included in the system for such psychophysical applications as perimetry and electrophysiological applications as multifocal electroretinography. The stimulus module can also provide an additional fixation target.

One accomplishes eye motion stabilization by locking a tracking beam onto a retinal feature and processing the back-reflected signal from that tracking beam. Robust lock has been achieved on many different natural retinal features, including blood vessel junctions, hypopigmentation, foveal pigment, and the bright lamina cribrosa within the optic-nerve head. The lamina cribrosa is an especially appropriate feature for tracking because it is present in all eyes, although the shape and degree of contrast variation with respect to the surrounding disc tissue varies widely from individual to individual. The TSLO tracking module includes a confocal tracking reflectometer and two pairs of scanners (x- and y-axes galvanometer-driven mirrors). A 25.4-mm fl lens 592 collimates the source beam 576 from a lowpower, multimode fiber-coupled (200-μm diameter core), 880-nm, surface light-emitting diode (PD-LD, Inc.).

Another 25.4-mm fl lens 588 focuses the detector beam 572 onto a multimode fiber-coupled (200-μm diameter core) APD (Hamamatsu Inc.). The entrance and exit pupils of the confocal reflectometer, determined by separator 616, are ~2 and 9 mm, respectively. The source fiber size (200-μm core diameter) and optical magnification determine the size of the tracking beam on the retina (600 μm or ~2 deg with the Volk 66 D ophthalmoscopic lens). The detector fiber (200-μm core diameter) acts as the confocal aperture. Smaller diameter fibers result in decreased coupling efficiency, but a greater degree of confocality (e.g., better depth resolution and improved lateral contrast) within the confines of the optical aberrations present in the eye. It is clear from the confocal aperture size that the depth resolution is finer for imaging than for the tracking reflectometer. The tracker beam power measured at the cornea is ~25 μW. A 840-nm long-pass dichroic beam splitter 556 (Omega Optical, Inc.) combines the tracker beam into the imaging beam path. The two paths are made paraxial and parfocal.

The first pair of resonant dither scanners 544, driven at 8 kHz with constant amplitude and fixed phase relation (Electro-Optical Products Corporation), is used to trace out the tracking beam on the fundus. The second pair 540, galvanometer-driven tracking mirrors (Cambridge Technology, Inc.), are driven from the output of the control loop and move all beam paths (e.g., the image raster) as the eye moves. By placing the tracking galvanometers near the conjugate to the eye's axis of rotation (between the pupil and retinal conjugates), one also achieves partial pupil tracking simultaneous to retinal tracking. Moreover, high-speed algorithms can eventually be employed to correct higher-order motion such as rotation about the optical axis.

Figure 13:
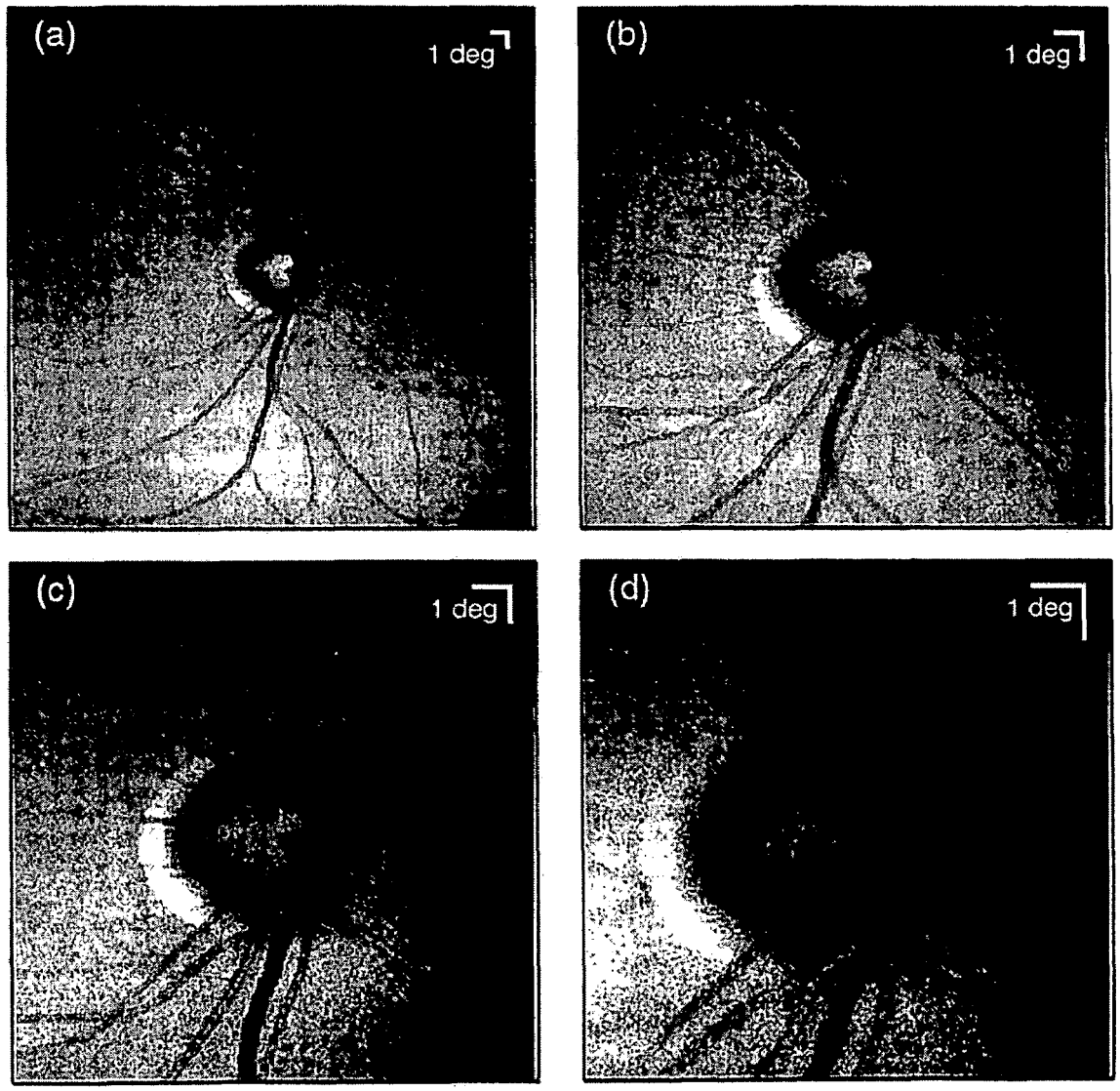
FIGS. 13A-13D illustrate the broad range of the field of view for a series of opthalmoscopic lenses.

Several different opthalmoscopic lenses 508 (Volk, Inc.) can be used in the TSLO, depending on the magnification required for the application. FIGS. 13A-13D illustrate the broad range of the field of view for the system from 28.6 deg for the 66-D lens (FIG. 13A) to 9.3 deg for the 20-D lens (FIG. 13D), using single video frames. FIG. 13B is a 40-D lens, and FIG. 13C is a 30-D lens.

The two-dimensional retinal tracking system developed by Physical Sciences Inc., and which can be used with the SLO, can use confocal reflectometry and digital signal processing (DSP) control loops to steer a diagnostic or therapeutic beam to correct for transverse motion. For example, the tracking beam is dithered in a small circle around a target feature by a pair of scanners driven at their resonant frequency (8 kHz) and separated in phase by 90°. The light reflected from the target at the image plane passes back to the reflectometer where error signals are generated. The tracking target is chosen to be any region with differential brightness from the background. The light contrast between target and background is therefore an important system performance parameter. By use of phase-sensitive detection, the position error vector between tracker beam and target is found. When the dither circle is displaced from the target, the reflectometer output can include in-phase and quadrature components of the dither drive signals. For example, if the target moves along the x axis, the reflectometer output is in phase with the x-dither drive signal and out of phase with the y-dither drive signal.

Figure 14:
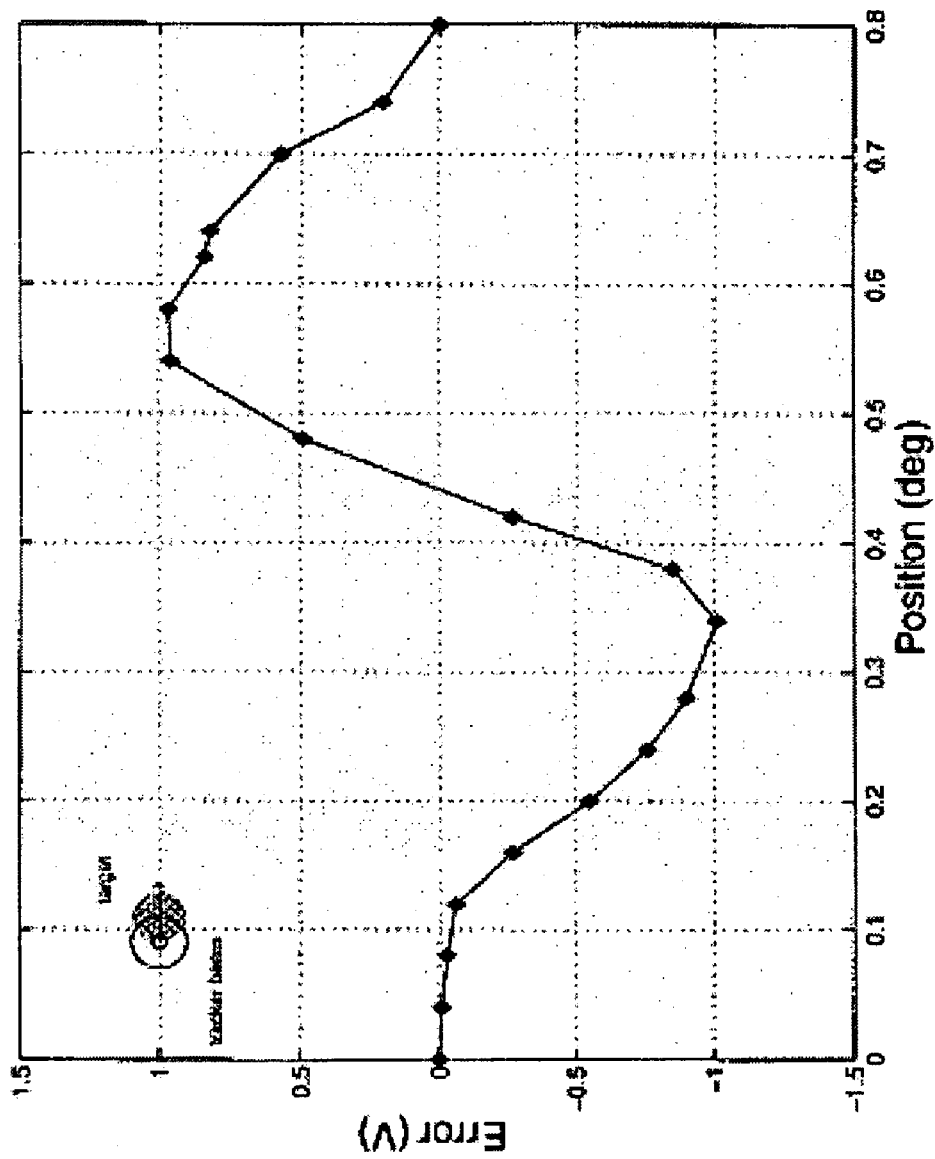
FIG. 14 illustrates the signal processing for a retinal tracking device.

The output of the dual-channel lock-in amplifier is a dc signal (with amplitude proportional to the displacement) on the x-error channel, and no signal is present on the y-error channel. The error signals are fed back into an algorithm that controls the signals that drive the tracking mirrors. As transverse motion is detected, the error signals cause the tracking mirrors to shift to the new position and thus keep the tracker beam locked on the target. FIG. 14 illustrates the tracker signal processing.

Figure 15:
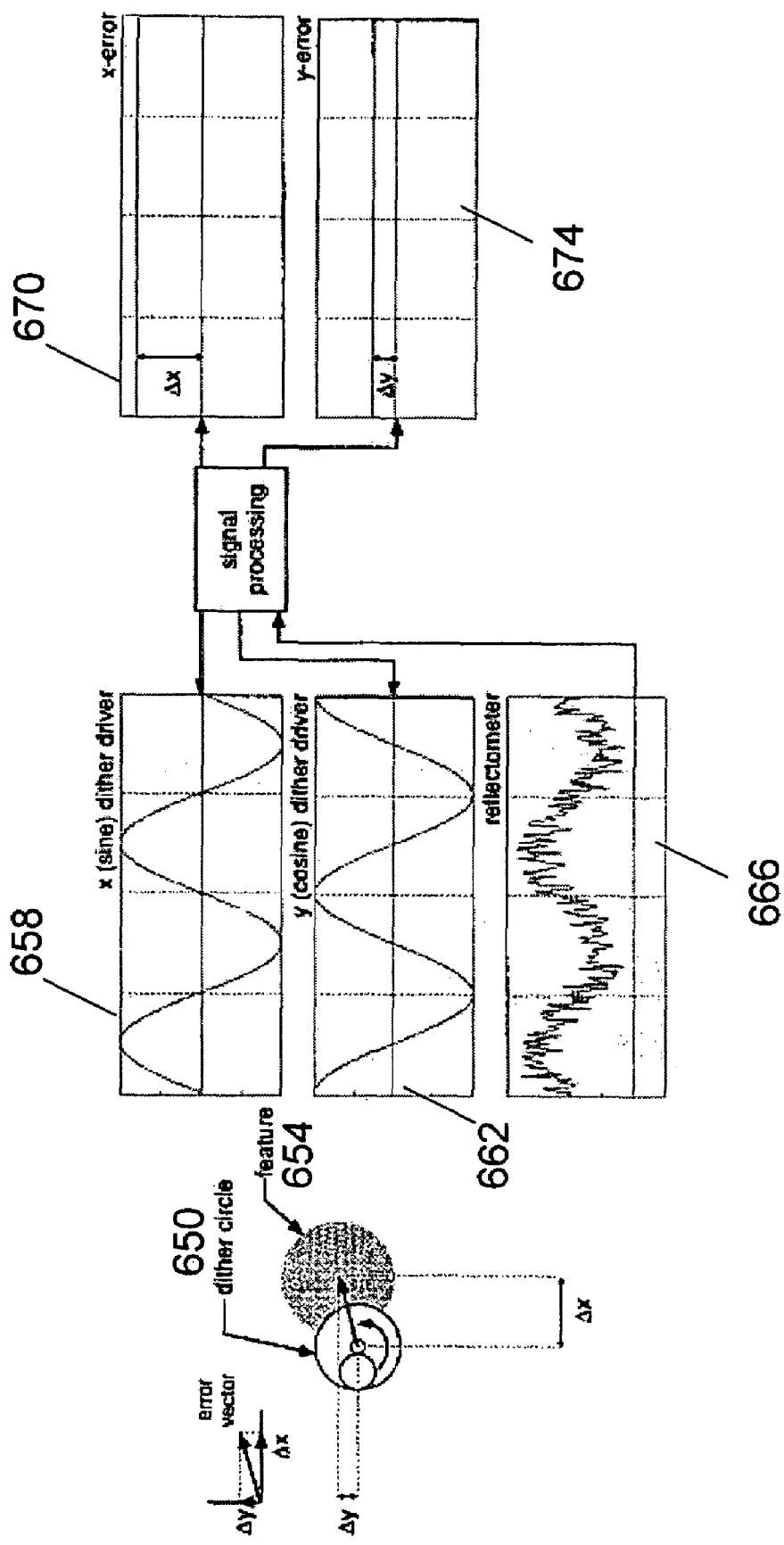
FIG. 15 depicts the error signal generated from sweeping a tracking beam across a target in the x direction.

FIG. 15 shows the operation of signal processing when the a dither circle 650 is oscillated about a reference feature 654. The dither circle 650 has an oscillatory motion in a first direction 658 and a second direction 662 with a first phase and a second phase, respectively. In addition, an output signal 666 of the reflectometer is shown as a function of time. The phase of the output signal 666 depends on the direction in which the image of the reference feature 654 is displaced from the dither circle 650.

A corresponding first direction control signal 670 and a second direction control signal 674 after signal processing 678 are also illustrated. The direction control signals are proportional to an error in the first and the second direction. When the dither circle 650 is centered and locked onto the image of the reference feature 654, the direction control signals are null. Signal processing can also yield a tracking lock signal, although it is not illustrated. The tracking lock signal can indicate that the dither circle is locked onto the image of the reference feature When the tracker beam is locked onto a feature, the feedback control loop drives the error signal back toward the zero crossing (null). The system loses lock if a large and rapid movement (exceeding the system bandwidth) causes the beam to become displaced from the target (e.g, the dither circle 650 is outside the image of the reference feature 654) such that the error signal is no longer on the slope between the minimum and the maximum. The output signal 666 also becomes low, which indicates a loss of tracking. The signal processor generates null direction control signals and a null tracking lock signal as well.

Figure 16:
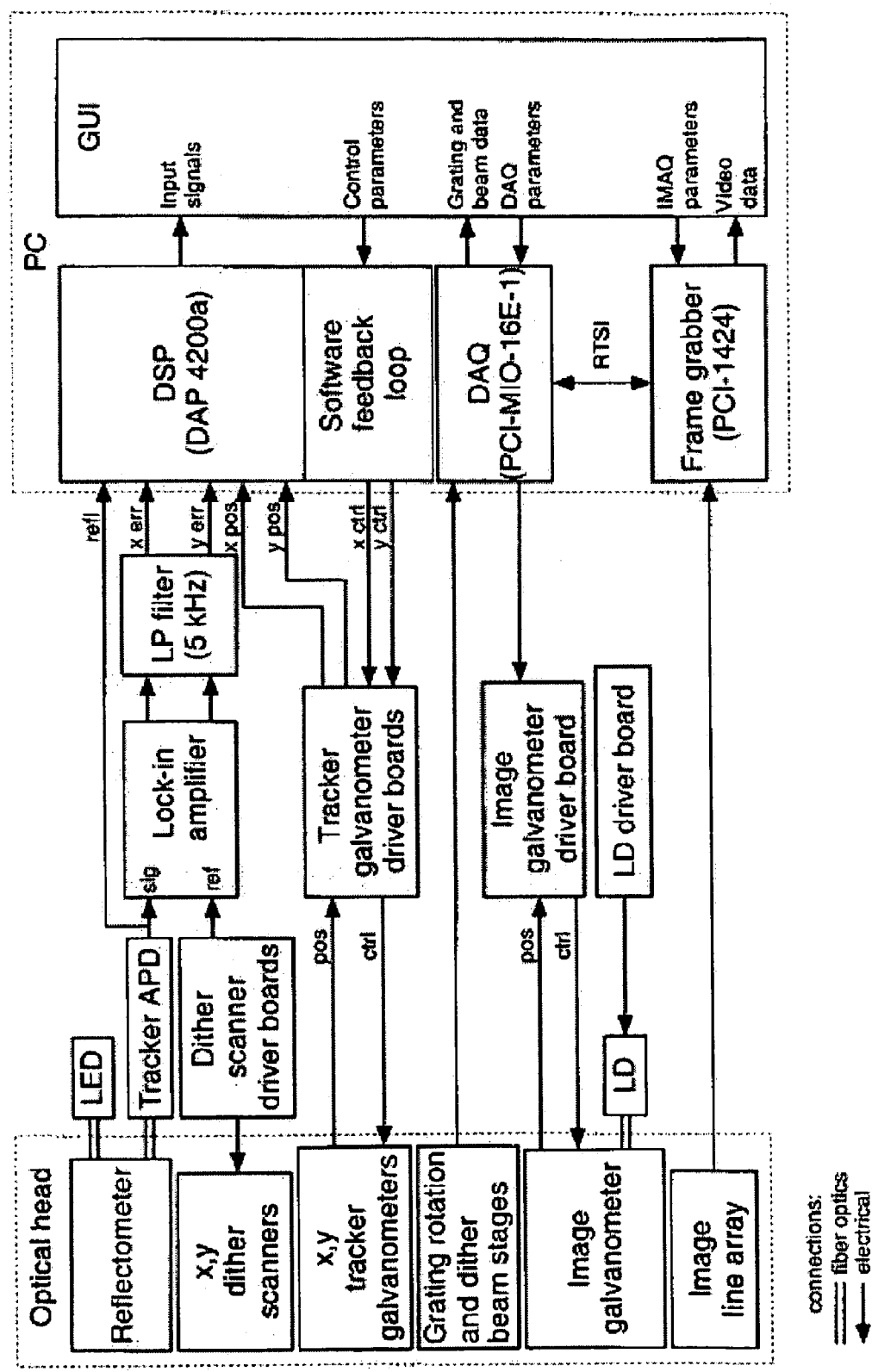
FIG. 16 shows a block diagram of the TSLO electronics, hardware, and software interface.

A block diagram of the TSLO electronics, hardware, and software interface is shown in FIG. 16. Instrumentation boxes can be constructed for the TSLO that contain the driver for the resonant dither scanners phase locked at a single frequency (Electro-Optical Products Corporation), closed-loop galvanometer control boards (Cambridge Technology, Inc.), a laser diode driver board (ThorLabs, Inc.), an APD detector and amplifier board (Hamamatsu, Inc.), a dualchannel lock-in amplifier (Scitec Instruments, Ltd), analog signal filters (Frequency Devices, Inc.), fibercoupling optics, and power supplies and voltage regulators to drive the electronics. The tracking galvanometers use only the servo amplifier, position detector, and resonant frequency notch filter on the driver boards. A real-time programmable DSP board can be used for feedback control rather than the fixed closed-loop control electronics on the galvanometer driver boards for two reasons. First, the control loop that resides on the boards uses position feedback rather than the desired feedback with the optical error signals generated separately from the APD and lock-in amplifier. Second, the DSP software control provides a large degree of flexibility in adjustment of control parameters. This is especially important for the TSLO because of the large variability in fundus reflectivity and feature size and shape.

The control computer can include real-time DSP, data acquisition (DAQ), and digital frame-grabber boards. The real-time DSP, or data-acquisition processor (DAP 4200a, Microstar Laboratories, Inc.) is used for the control algorithm to provide the flexibility in implementation necessary for a research tool. In addition to analog input-output, timers and an interface to the PC, the DAP board contains an embedded processor that allows the control loop to proceed without interruption while the host PC handles the user interface. The DAP operates with a 16-kHz loop rate, sufficient for closed-loop control at the required bandwidth. The reflectance, lock-in error, and tracker mirror position signals are input to the DAP board, and the control signals to the tracker mirror driver boards are output from the DAP board.

The DAQ board (PCI-MIO-16E-1, National Instruments, Inc.) is used to generate the signal to control the image scanner, as well as receive static tracker beam location and grating rotation signals. Within the TSLO optical head, there are three mechanical adjustments: the first and the second control angle and tilt for the entire confocal reflectometer stage to steer the tracker beam on the fundus relative to the image raster, and the third controls rotation of the stage on which the grating is placed. Potentiometers are used to convert the tracker beam location and grating rotation to electrical signals for input to the DAQ. The monochromator can include servo or step-motor-driven rather than manual-driven grating stages, as well as focalplane depth scanning for the SLO.

A digital frame-grabber board (PCI-1424, National Instruments, Inc.) is used for image acquisition. The frame grabber generates and transfers the master clock (at 20 MHz), line readout (generally 15 kHz), exposure control and gain signals to the digital line-array detector. The line readout rate is set by the image scanner through the DAQ board. The framegrabber and DAQ boards communicate via a realtime system integration bus. All frame-grabber and DAQ driver functions are controlled from the graphical user interface (GUI).

The software used to control the TSLO consists of a feedback control routine, GUI, and input-output libraries used to generate and manage the communication pipes between the computer's host processor and the processor that resides on the DAP board. The communication pipes are used to send user-generated parameters from the GUI to the DAP and to send reflectance, position, and error signals from the DAP to the GUI for display and further signal processing. The GUI can be written in LabVIEW (National Instruments, Inc.), although other programming languages can be used.

In one embodiment, the feedback control loop algorithm moves the tracking mirrors in response to measured errors in a critically damped manner. A standard proportional-integral-derivative (PID) algorithm is used for this purpose. The controller sends a torque (acceleration) signal to the scanners that consists of the sum of three terms. The term proportional to the measured error results in a spring-like response.

The integral of the measured error counters constant-offset torques and electronic offsets in the motor drive circuit. The derivative term, the time rate of change of error, damps oscillations that result from the spring response. In addition to the PID loop, the control software includes code for automatic correction of output biases that result from offsets generated in the galvanometer boards. The automatic output bias correction averages the output when the tracker position is under mouse control and uses that as the initial offset when the user releases the mouse to initiate tracking (drag-and-drop mouse control). Although the output biases can be nulled automatically in the software, input biases that result from detector and lock-in electronics that cannot be automatically nulled can be used. These offsets are corrected by passing, in addition to the PID parameters, offset values from the GUI to the control software.

Figure 17:
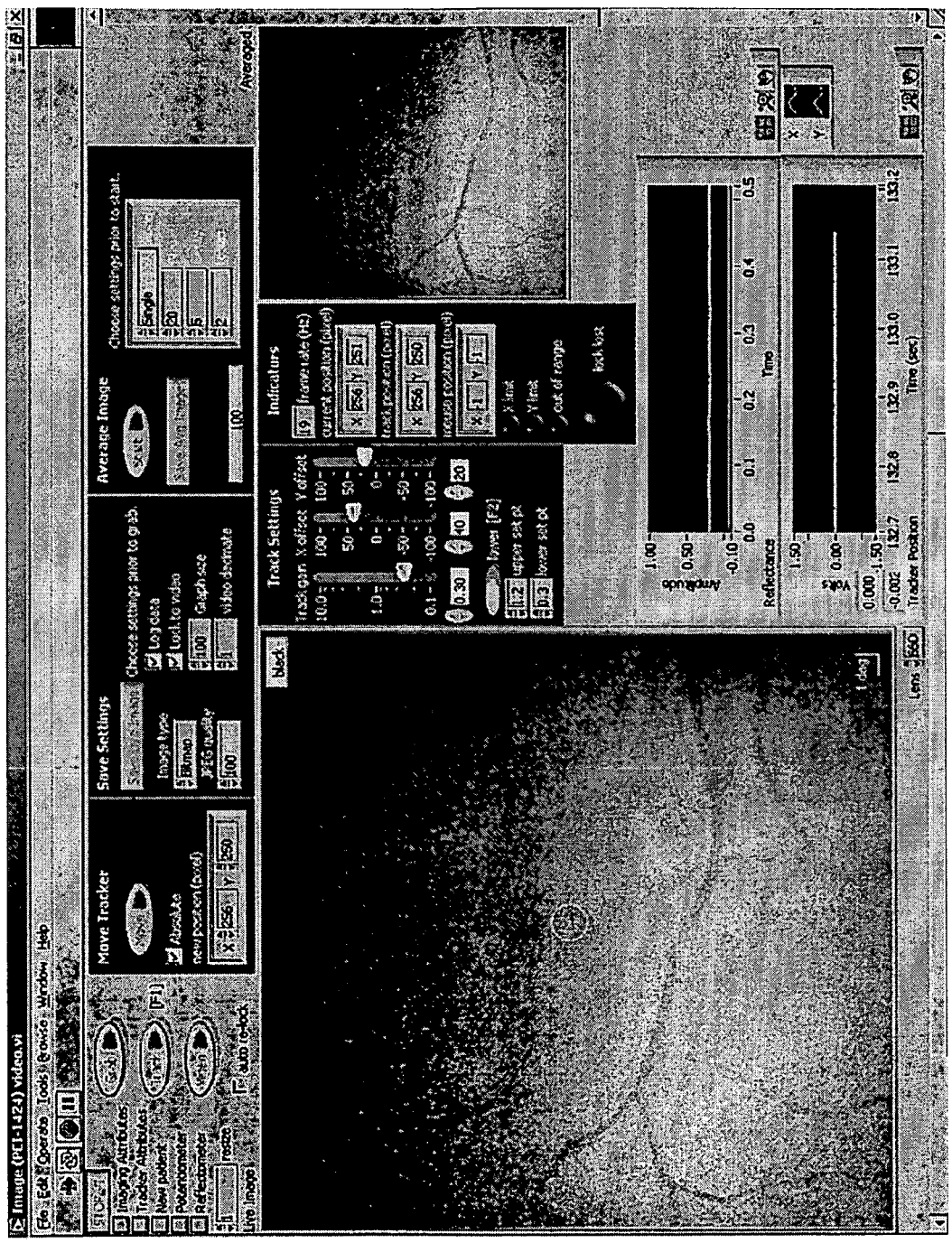
FIG. 17 shows the graphical user interface for an exemplary TSLO.

FIG. 17 shows a screen print of an exemplary GUI, which can include functions for image-acquisition setup and display, all parameter calibration, and all signal control and processing beyond the control algorithm described above. Tracking is initiated from the mouse in a drag-and-drop manner to locate a suitable tracking target. Dialog boxes are used to input and manage patient information, all image-acquisition and image-processing parameters, all control parameters, and calibration and analysis of the tracker beam position and grating rotation signals. The information and settings controlled with the dialog boxes can generally be considered "set once and forget." Any settings that require continual update from the user are set from the front panel of the GUI. For example, although PID control parameters are set from a dialog box, gain and offset slides allow the user to rapidly adjust tracking parameters from the front panel. When locked on a target, the gain slide can adjust the feedback gain. Increasing gain yields stiffer tracking but reduces damping, whereas decreasing gain improves damping at the expense of robust tracking. The ideal gain is one that gives maximum stiffness without oscillations characteristic of the underdamped condition. Thus, the user can adjust the gain slide to the point where oscillations are just minimized to locate the critically damped condition.

The GUI can also include algorithms for real-time image averaging and automatic relock. Image averaging can be run in three modes:

1. single, in which n frames are averaged and then displayed,
2. continuous, which continuously updates and displays the average of n frames, or
3. running, which displays a running average of the previous n frames The automatic relock algorithm uses operator-defined limits of the reflectometer signal to determine the occurrence of loss of lock, upon which the system automatically disengages tracking, returns to the last position where tracking was initiated, and reinitiates tracking. For example, when a subject blinks, the reflectometer signal decreases outside of the set range, and the software returns the tracker mirrors to the last locked position. Lock can be reestablished in less than 1 sec if the subject's eye has not moved considerably during the blink. Tracking is also turned off if for any reason the tracker beam goes outside of a user-defined field of regard. Finally, the user can save compressed and uncompressed images, uncompressed videos, and binary data files for further analysis and processing.

In one embodiment, for monitoring retinal blood flow, a 25-μW, 880-nm LED tracking beam is dithered on a retinal feature (e.g., the lamina cribrosa) and detected with a confocal reflectometer. The processed reflectance signals can be used to create error signals proportional to eye movements and fed back to an x-y galvanometer-driven mirror pair, as described above. A 300-μW, 780-nm laser illumination beam can be fanned out on the retina and detected confocally with a linear image sensor or linear diode array. The transverse resolution is approximately 40 μm. The estimated depth of focus is approximately 1 mm for the quasi-confocal LSLO imaging, but this parameter is somewhat arbitrary and is not the same as the usual confocal parameter for SLOs.

Videos can be acquired with a linear detector with a line rate of 7.5 k lines/sec (Physical Sciences Inc.). The videos can be reproduced as a series of still photographs of the eye. The 7.5 k lines/sec line rate can preclude measurement of the peak velocities in large vessels, but can allow for higher resolution images of retinal perfusion. An alternate image sensor with a line rate up to 39 k lines/sec (Fairchild Imaging Inc.) can be used to measure peak arterial velocity. In the optic nerve head, where the major vessels turn, the peak Doppler frequencies can remain above the bandwidth limit of this instrument. In the conventional LSLO imaging mode, the line is swept over the retina at a rate that can exceed 60 frames/sec.

As described above, an algorithm can be implemented to automatically re-lock the system after a subject blinks. The subject is instructed to look at a fixation target. If lock is lost, the tracking system can wander or slew rapidly depending on bias settings because the closed loop-gain of the servo is high. When the tracking system detects an out-of-bounds target reflectance or tracking angle, tracking is suspended. After a brief delay to allow for the blink to be completed, the tracking mirrors are re-positioned and a re-lock command is issued.

Figure 18:
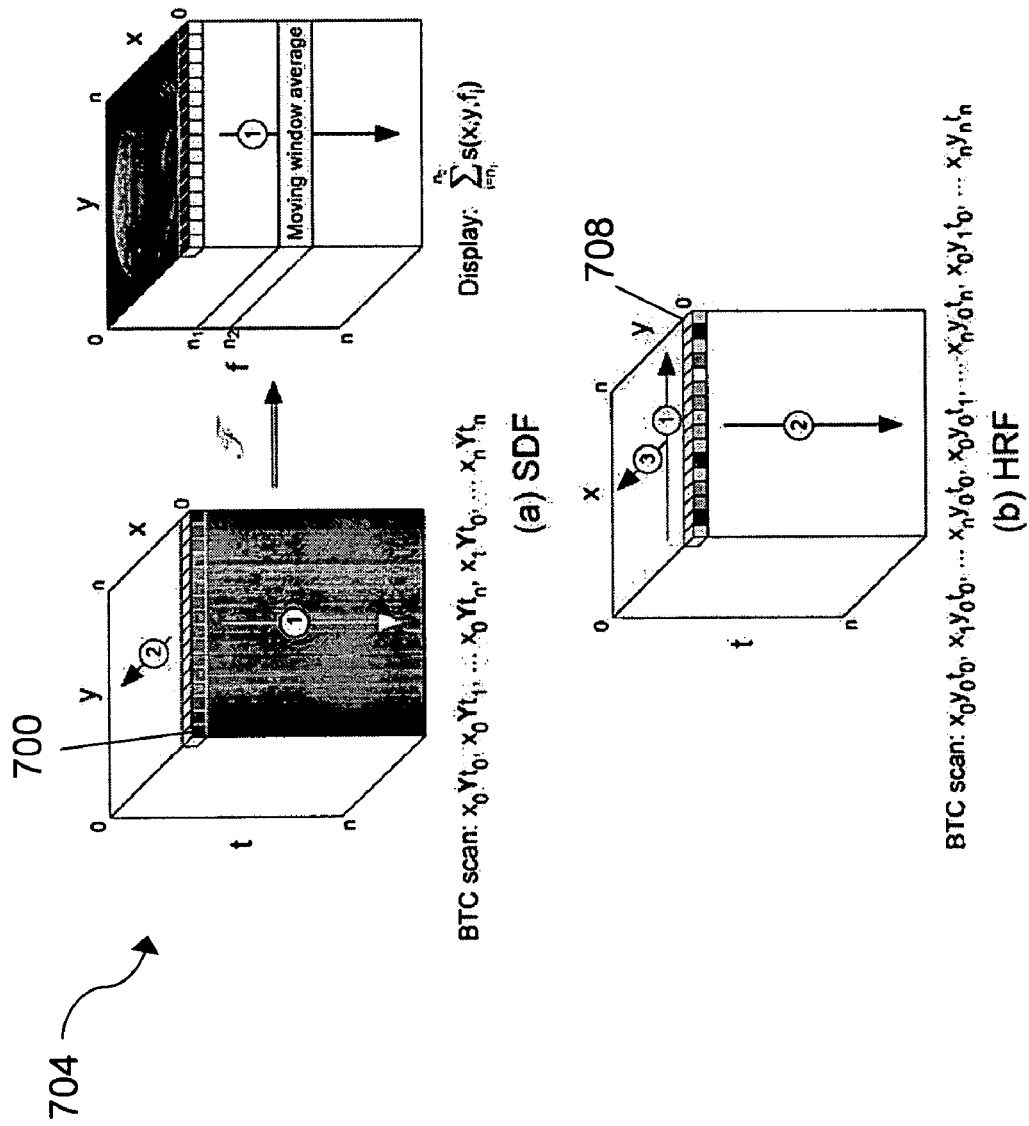
FIGS. 18A and 18B illustrate a diagrammatic comparison of the SDF and HRF techniques, respectively.

By performing slow infrared line scans, tracking the eye, and re-locking after blinks, frequency-resolved images of retinal flow can be obtained. In one embodiment, this SDF technique can be used as a fast and efficient Doppler image capture methodology. FIGS. 18A and 18B illustrates a slow scan technique for SDF (A) and for the HRF (B). The order of the BTC scan sequence is numbered on the diagram. The scan equation is shown below the diagram for each type. After Fourier transformation, the data cube can be displayed as a video where individual frames are created by binning individual frequencies with a moving window. This is described in more detail below.

In one embodiment, the retina is illuminated with a line of light at a first position and a second position. The retina need not be illuminated in these positions simultaneously. A first plurality of images of the retina is recorded at the first position along, for example, the y-axis in FIG. 18A. Each image can be represented as an individual block 700. Each image is recorded for a first set of successive time periods (represented by arrow 1 in FIG. 18A) This forms a first spatial-temporal image plane (e.g., a first y-t plane). A second plurality of images is recorded at a second position along the y-axis. Each image is recorded for a second set of successive time periods to form a second spatial-temporal image plane (e.g., a second y-t plane). To record the second plurality of images, the line of light can be stepped along the x-axis to a second position.

Using a signal processor, the spatial-temporal image planes (e.g., two or more) to form a three-dimensional image 704 of the retina. The temporal dimension or time axis represents the flow of blood in the retina. The temporal dimension or time axis can also represent a rate of change of the retina. Each of the spatial-temporal image planes can have N spatial pixels and N temporal pixels. In one embodiment, the retina is illuminated with a line of light at N positions to form N spatial-temporal image planes. An image cube with dimensions of N×N×N can be formed. The three-dimensional image can be processed with a Fourier transform (represented by the cursive F in FIG. 18A) to yield a power spectrum of each image pixel.

For a linear array with 512 elements (larger or smaller linear array can be used depending on the application and or optical configuration of the LSLO), the linear array is read out 512 times at one line on the retina and stored as a single BT image plane (i.e., y-line vs. time) before the next line is scanned. Each BT plane of the image cube therefore comprises an image of 512 spatial pixels by 512 or more temporal pixels. Since the linear sensor integrates the light collected, a nearly continuous temporal profile is obtained at each pixel for the duration of the BT scan. The line rates for the respective linear sensors give inter-line times of 133 μs and 26 μs, and the integration duty factor is approximately 80% of these values. This significantly diminishes the susceptibility to aliasing. In a slow C-scan, 512 such BT planes are captured across the fundus, taking 35 seconds to complete a full BTC image cube at 7.5 k lines/s, or 6.7 seconds at 39 k lines/sec. Two scans in immediate succession can be performed, so that blanking that occurs during blinks can be overwritten by the valid data of the twin scan. Scans can be precisely repeated after any intervening interval by simply locking onto the same retinal feature.

During data acquisition, a subject is asked to fixate on a bright green target with the fellow eye. A dull red raster is visible during normal TSLO imaging. When the SDF scan commences, a bright red vertical line can be seen moving slowly across the visual field (e.g., left to right, although nasal/temporal, superior/inferior and other configurations can be used as well). The passage of the line over the fovea can induce some momentary undesirable nystagmus and vergence/near triad responses. While the tracking system can compensate most of these motions, internal (non-stabilized) fixation can be used.

In one embodiment, the SDF technique measures Doppler power fluctuations in a sampled tissue volume, and this method of line-scanning and imaging enables wide-field 2D maps to be constructed where each point in the image contains a Doppler spectrum (Doppler power spectral density vs.

frequency). To apply a meaningful interpretation to these data, a method of analysis, normalization, scaling and display is used.

For example, after image cube acquisition, a Fourier transform, e.g., a fast Fourier transform (FFT) can be used to extract the full power spectrum at each image pixel. Because the blood flow is related to the "AC" parts of the spectrum (frequency, f>0), and the "DC" part is the average image brightness, it is convenient to normalize the power spectrum by the DC value. This removes the variability across the image associated with beam power and average reflectivity of different portions of the retina.

To create frequency videos, the spectra at each pixel can be binned with several different windows, including one with a fixed size and one with octave increments (2, 4, 8 . . . ). The processing can use an overlapping moving window with an increment and halfwidth of 8 and 16 frames (117 and 234 Hz for the PSI camera), respectively. After binning, the individual frequency frames can be linearly contrast-stretched between minimum and maximum image intensity in 8-bit image planes (e.g., using a micro-processor). Videos constructed using this type of processing can reveal the transition of flow rates and vessel patterns from the smallest to the largest size scales, and can evoke the visual effect of early phase angiography. The videos can also be used as a means of interpreting the data, which more fully exploits the improved dynamic range and signal-to-noise ratio, beyond, for example, conventional "volume, flow and velocity" maps associated with the HRF.

As shown in FIG. 18B, HRF sample each pixel 708 individually to form a line, and then moves to a second line to begin recording each pixel individually for that line. HRF can sample at a rate of 4 k lines/sec. As a result, a significant impact of this lower line rate—determined by the mechanical hardware—is that the Nyquist Theorem limits the maximum frequency detected to 2 kHz. Even more important is the fact that the duty cycle can be an extremely small percentage ($\frac{1}{256}$) contingent upon the number of pixels in the line. This detection approach based upon sampling leads to aliasing and consequently, velocity errors. Moreover, since tracking is not employed in the HRF, frequencies below 125 Hz are disrupted by motion and not processed or displayed. Eye motion also prevents acquisition of even moderately-sized and sampled retinal fields. The BTC scan dimensions of the HRF are 256×128×64. The TSLO with scan dimensions of, for example, 512×512×512 has 16 times the spatial resolution, and 4 times the temporal resolution. Depending on the linear sensor, the TSLO has 1.875 or 9.5 times the accessible peak Doppler frequency, and extends to as low as 14 Hz.

EXAMPLE OF THE TSLO IN SDF MODE

The TSLO with SDF mode was used for wide-field blood flow imaging of seven normal subjects and four patients recruited from a retinal practice. Videos created from two normal subjects and two patients are shown below. The videos can be displayed at 10 frames/sec, but each frequency bin can be viewed by stepping through frames in Windows Media Player or Apple Quicktime. For the purposes of this disclosure, individual frames of the video are reproduced in the figures. Each frame is a record at a particular frequency or over frequency range. The first frame of each video is the reconstructed fundus image created from the DC value.

Figure 19:
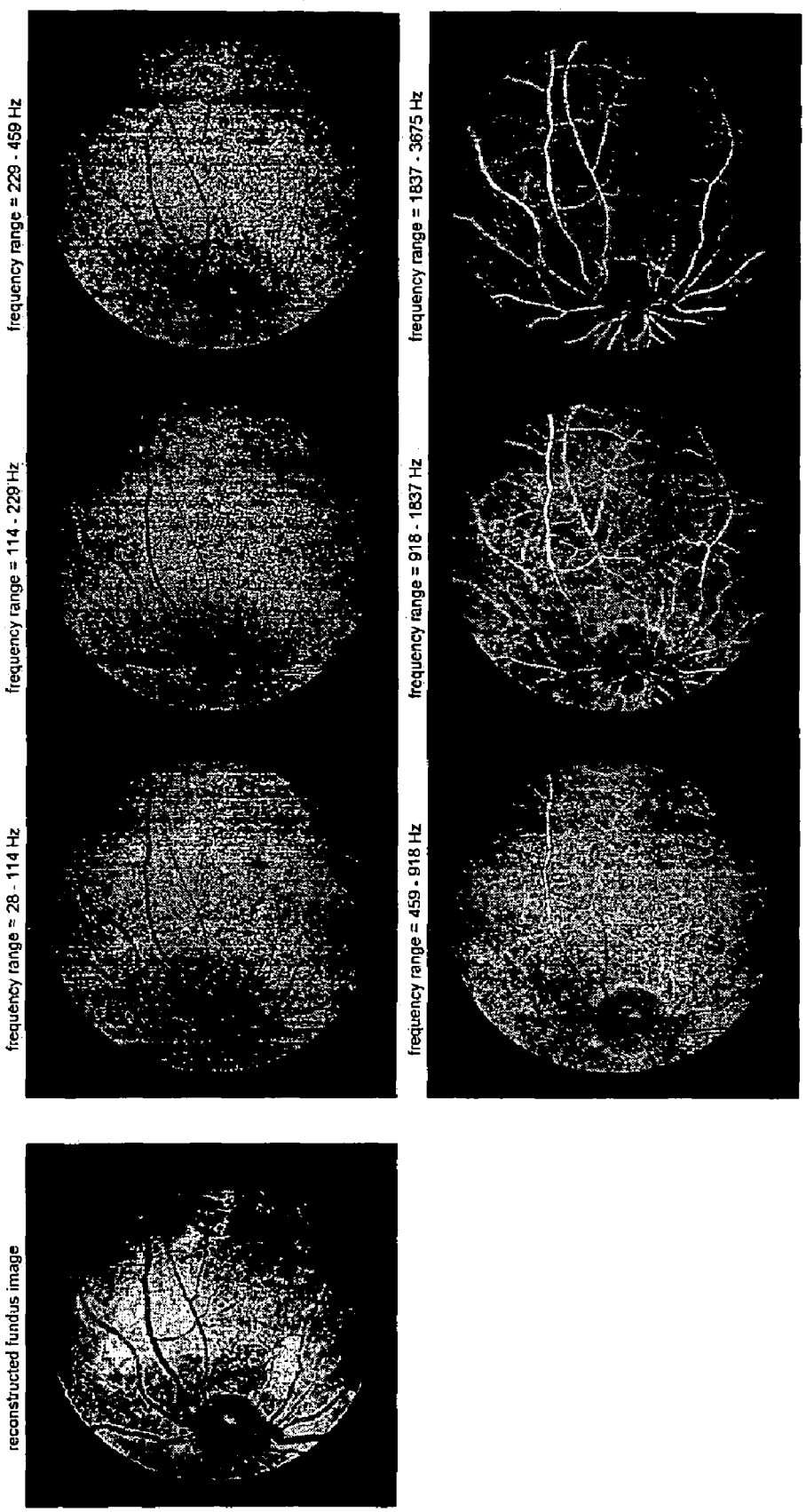
FIG. 19 shows blood flow images of a healthy 24 year old subject.

FIG. 19 shows a blood flow video for a healthy 24-year old subject. The vertical line noise at the lowest frequency bin is caused by small amplitude (<1 pixel) transient tracking stability artifacts. In all images, dark vertical bands near the fovea (only in undilated subjects) are due to nystagmus invoked by occasional fixation on the scanning line as it passes across the fovea, causing some vignetting by small pupils. Such effects can be adequately compensated by DC normalization. Young healthy subjects often show bright specular reflection, presumably from the nerve fiber, which are DC only and affect Doppler images through the normalization.

The foveal avascular region is clearly visible at low frequencies. In the lower frequency bins (f<400 Hz), or the "perfusion range," flow in the retinal capillary beds and the choriocapillaris creates a bright field that is shadowed by the overlying retinal vessels, which happen to be dark in these frequency bins. This implies that the choroidal contribution to the flow maps can be attenuated by the RPE in darkly pigmented eyes, and perhaps by the focus and depth of field of the quasi-confocal imaging system. In middle frequency bins (f=400-1000 Hz), very small retinal vessels emerge, as well as pronounced peripapillary flow. At the highest frequencies (f>1000 Hz), the small vessels gradually fade and only the signal from the largest vessels in the retina and choroid can be detected. Note also the change in the reflectance of the lamina cribrosa as the frequency increases.

Figure 20:
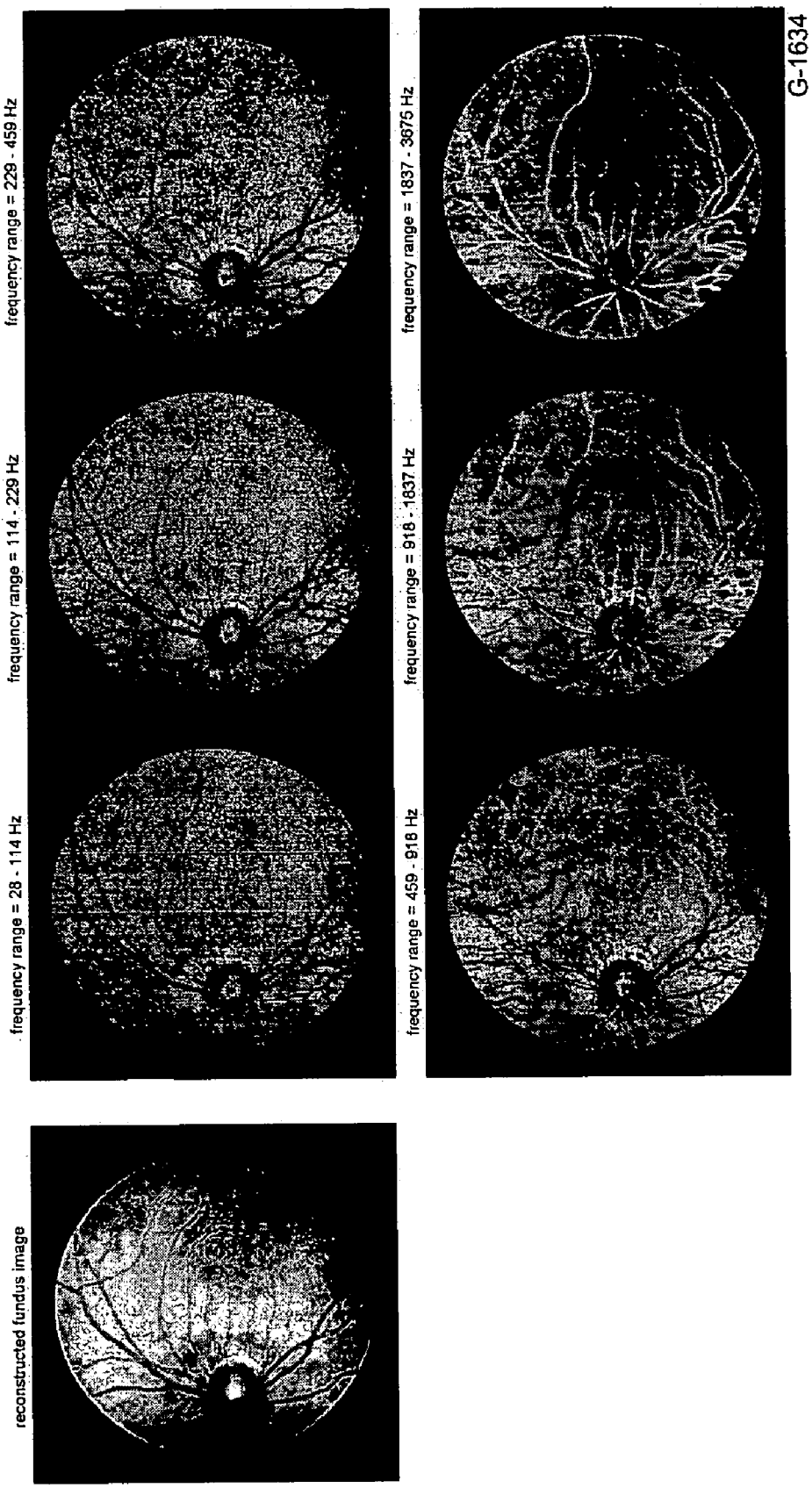
FIG. 20 shows blood flow images of a normal subject with light pigmentation.

A normal subject with lighter pigmentation shows much more choroidal flow detail in FIG. 20. This subject was highly myopic, accounting for the larger variation in focus across the field in the reconstructed fundus image. The foveal avascular region is again apparent at lower frequencies. At higher frequencies, vertical banding caused by pulsatile flow (at about 15 lines per beat) is quite strong in this subject in the choroid visible below the retinal circulation. It is interesting to observe that very little of this pronounced choroidal structure is visible in the reconstructed SLO image. Intense pulsatile flow occasionally gives arteries a beaded appearance. The perfusion of the choriocapillaris is undoubtedly contributing to the perfusion maps, but it does not overwhelm the retinal signal.

Figure 21:
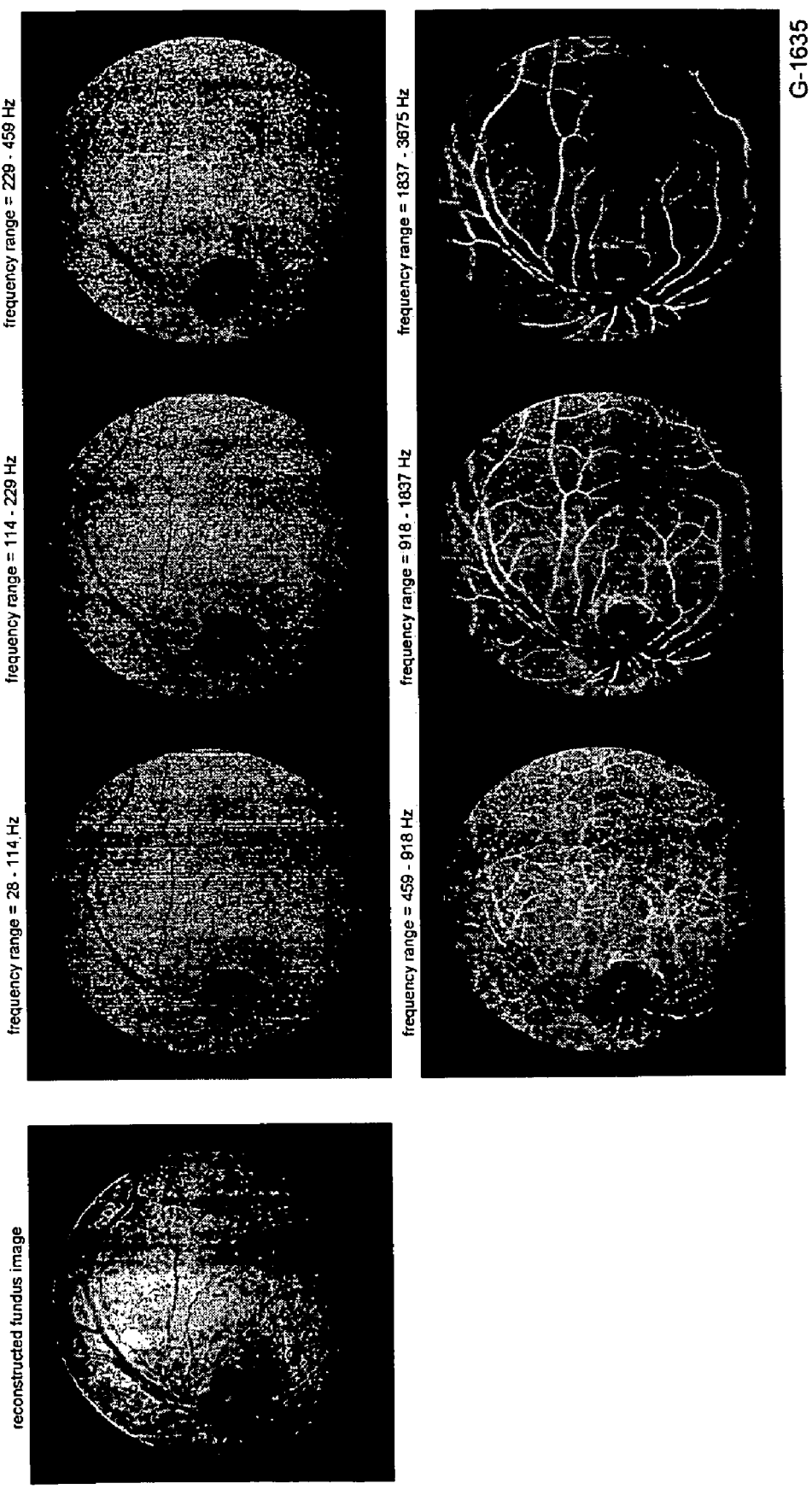
FIG. 21 shows blood flow images of a patient with central serous chorioretinopathy.

FIG. 21 shows a fundus image of a patient showing some sign of inflammation associated with central serous chorioretinopathy. However, perfusion appears to be normal in the low frequency frames of the video. Choroidal flow was difficult to observe, but visualization of medium-sized vessels at middle frequencies was more pronounced in this darkly pigmented eye.

Figure 22:
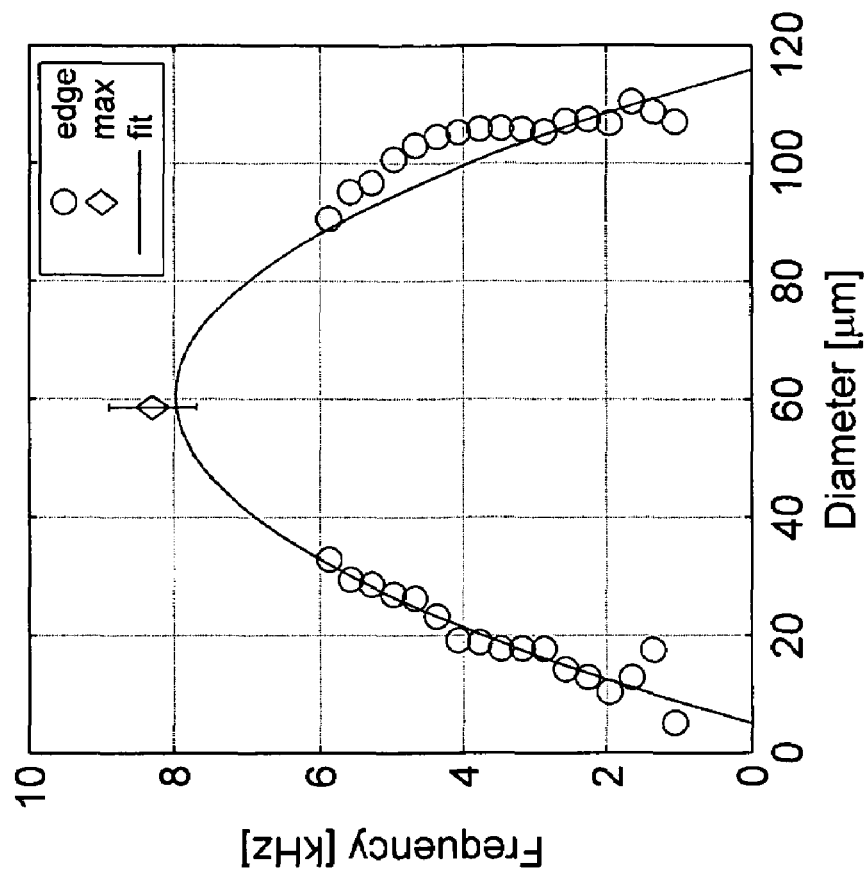
FIG. 22 shows a laminar Poiseuille flow measured in a major nasal retinal artery using a high-frequency, high-magnification scan.
Figure 22:
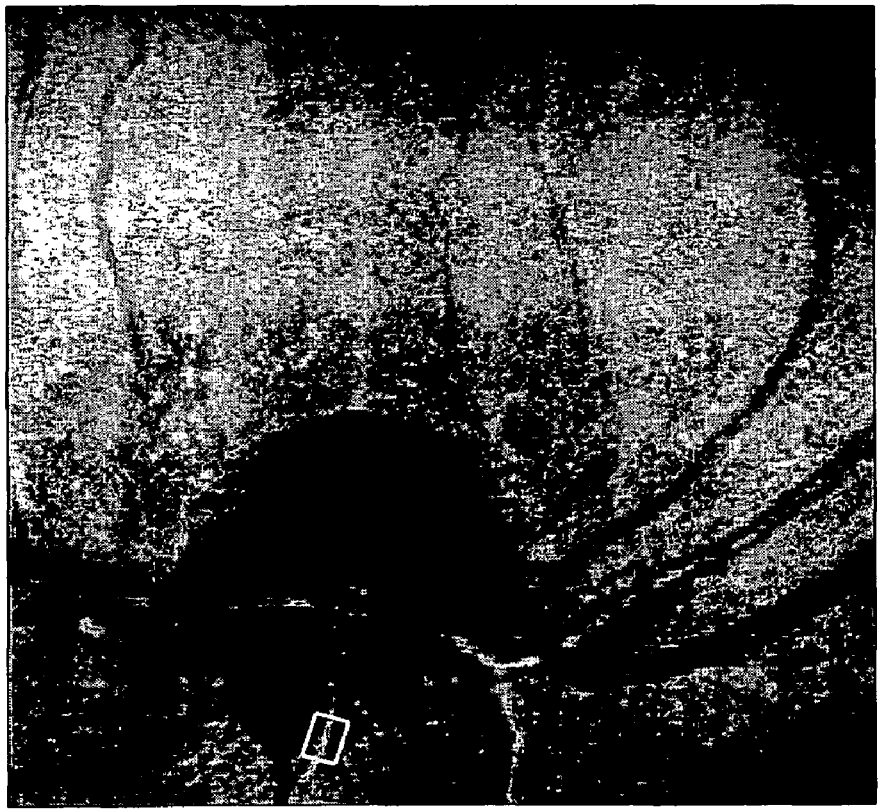

FIG. 22 shows an image of the same patient shown in FIG. 21. A higher-frequency (19 kHz), higher-magnification scan was acquired to determine the peak of laminar Poiseuille flow in the larger retinal arteries. At frequencies greater than about 15 kHz, the Doppler images appeared as featureless white noise at constant mean amplitude. This was taken to be the system noise floor and subtracted from the Doppler spectra. After noise correction and normalization, the average flow margin position (FWHM) for a small section of artery was measured at each frequency bin and the resultant data fit to a parabolic profile. At frequencies greater than 6 kHz, the flow signal was confined to a region smaller than the approximate resolution of the imaging system (~40 μm on the retina) and no further decrease in diameter was seen. The fit corresponds well with the frequency bin of the maximum resolvable signal in that vessel (8.3±0.6 kHz) and with previously reported measurements.

The estimated peak velocity, $u_p$, can be computed from the center frequency, $f_p$ as, $$u_p = \frac{f_p \lambda}{n \sin \theta_B} \quad (5)$$

where $\lambda$ is the laser wavelength, $n$ is the refractive index of blood, and $\theta_B$ is the estimated forward scattering half-angle of blood (~6 deg). For the peak shown in FIG. 22, $u_p$=4.6±0.4 cm/s (at the particular point in the cardiac cycle where the vessel was scanned).

Figure 23:
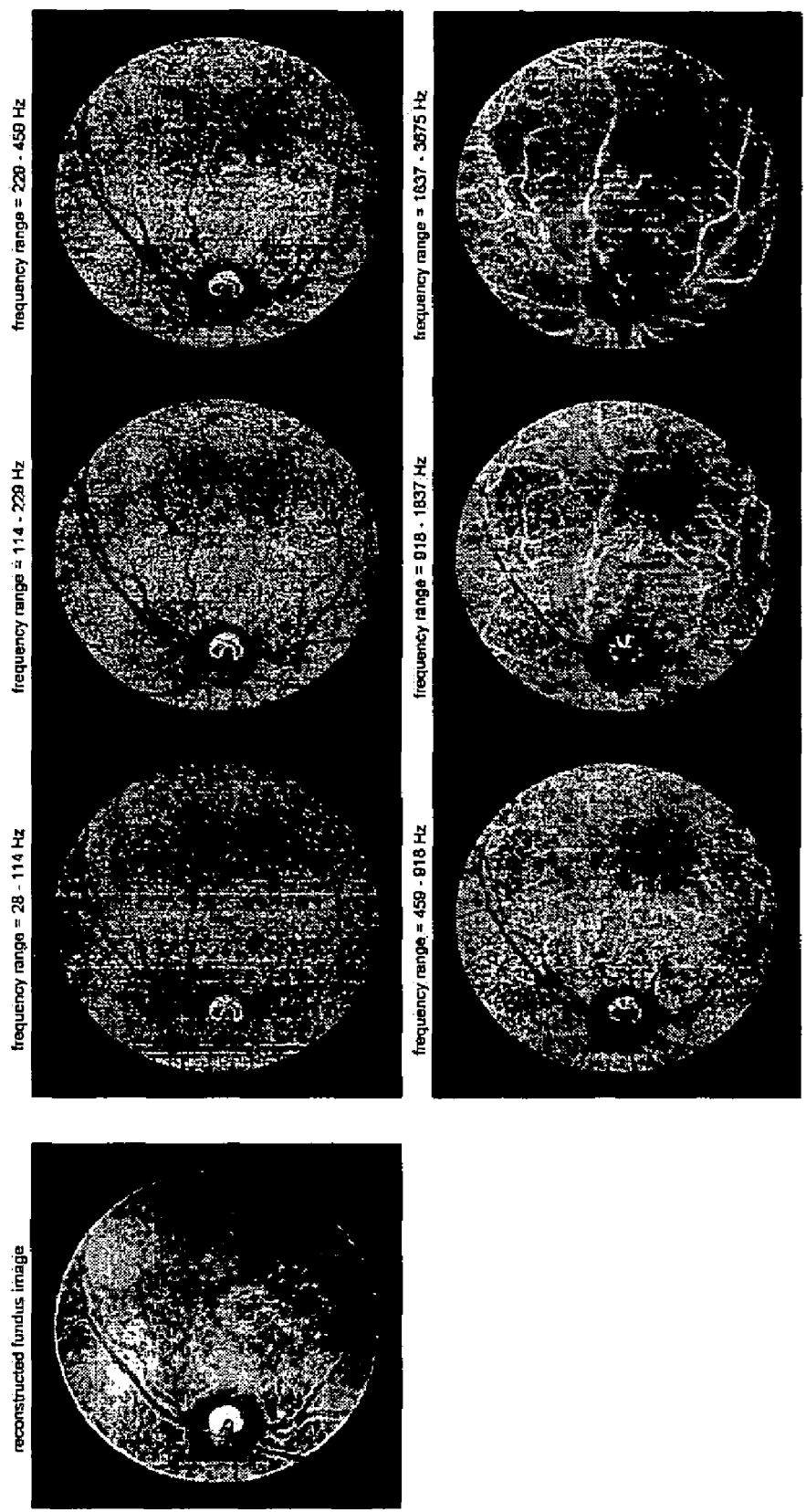
FIG. 23 shows blood flow images of a macular degeneration patient showing reduced perfusion in the macula.

FIG. 23 shows the blood flow video from a 68-year old patient with macular degeneration. Perfusion anomalies associated with apparent pathology are evident in the low frequency images, but also a large area of reduced perfusion temporally. The binned images show significant detail, even though the DC fundus image is not optimally focused through the relatively optically poor ocular media in this subject. The detail of the retinal vessels indicates the possibility for diagnosis of retinal-choroidal anastomoses and retinal vascular anomalous complexes associated with severe vision loss. Middle frequency peripapillary flow signal that was evident in all (younger) normal subjects was not visible in this patient.

Figure 24:
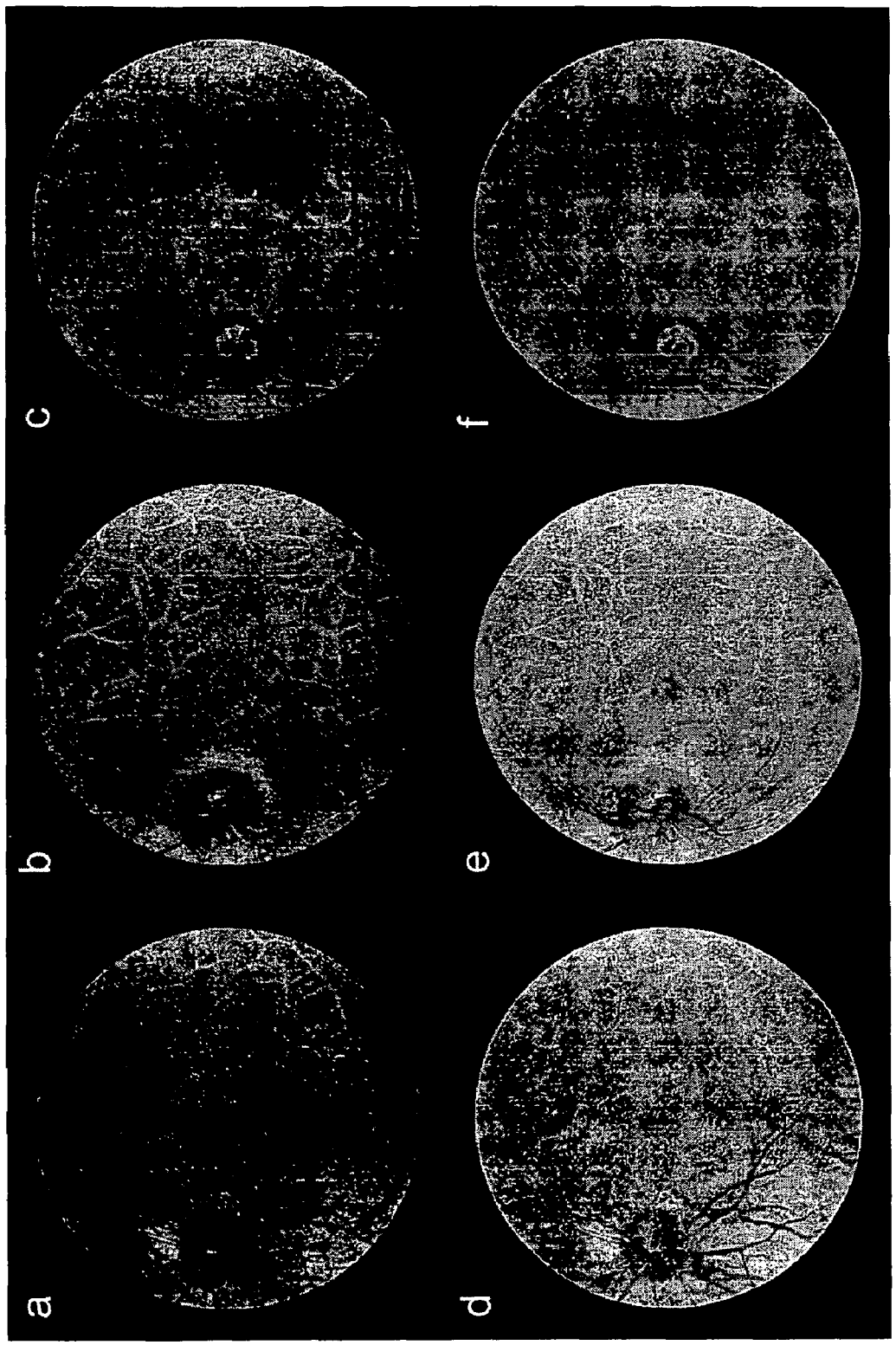
FIG. 24 shows a representation of a false color composite blood flow image for two patients.

FIG. 24 illustrates a black and white reproduction of an alternate representation of Doppler blood flow information using false color maps. To generate these maps, the transformed videos are averaged in three arbitrarily chosen ranges roughly representing capillary perfusion (f<400 Hz, red), middle flow in arterioles and venules (f=400–1000 Hz, green), and high flow in larger arteries and veins (f>1000 Hz, blue). The three bins can be DC-normalized, scaled and mapped into RGB colors, and then displayed.

Two different scaling techniques can be used. In the first, shown in the upper row of FIG. 24, each color plane is normalized and scaled individually (with the same linear contrast stretch in the videos above) so that the overall intensity range of each flow bin is matched in the composite image. This can create a black pixel where no flow at any frequency is present. Where high or low flow dominated, the pixel is more blue or red. This normalization and scaling scheme emphasizes vascualar anatomy, and can be used to compare structures within a Doppler image, but not from subject-to-subject because the Doppler band-to-band normalization is relative (normalized stretched spectrum scheme).

The second normalization technique is shown in the lower row of FIG. 24. In this representation, the maximum pixel value in each color plane is scaled to the average Doppler power per frequency bin. In this representation, the overall map color can be determined by which flow region dominated according to the true Doppler spectrum shape. Thus, the second normalization scheme can be used to make comparisons between subjects (normalized spectrum scheme). The spectral shape can provide information about the relative contribution of strengths of the binned Doppler power, so that flow anomalies are more pronounced.

FIG. 24 was created with data from the second normal subject and both patients presented previously. In the lightly pigmented normal subject, the higher choroidal flow (blue) is apparent in the nasal portion of FIG. 24A. In the patient with higher pigmentation, medium flow retinal vessels (green) are dominant (FIG. 24B). In both patients, the high pulsatile flow is also visible (FIG. 24B and FIG. 24C). Changes visualized with the second normalization technique (FIG. 24D-FIG. 24F) are dramatic in subjects with global blood flow defects (e.g., overall orange appearance of macular degeneration patient) compared to those without defect. However, care must be exercised in interpretation of this result. It is not yet known how poor image LSLO image quality in some patients affects the apparent distribution of Doppler power.

The partitioning of the flowmetry data into normalized frequency bins, which divides the images by vessel size and/or flow rate can be useful with the low noise levels achieved with the SDF scans. The sharpness of the reconstructed DC fundus images is evidence of tracking fidelity during the long scans. The perfusion images (f<400 Hz) have similar appearance and correspond to Doppler velocities less than approximately 2 mm/s. These images combine retinal and choroidal contributions. The remaining bins begin to reveal the various vessel size and flow speed echelons in the vascular tree, up to in-plane velocity component values of ~20 mm/s. In a large superficial retinal artery, a linear array sensor can be used with a maximum line rate of 39 k lines/sec to measure laminar Poiseuille flow and a peak velocity of ~5 cm/s.

While the invention has been particularly shown and described with reference to specific illustrative embodiments, it should be understood that various changes in form and detail may be made without departing from the spirit and scope of the invention as defined by the appended claims.

What is claimed:

1. A method of monitoring blood flow in a retina, comprising:
    illuminating the retina with a line of light at a first position and a second position;
    recording a first plurality of images of the line of light on the retina at the first position and a second plurality of images of the line of light on the retina at the second position, each of the first plurality of images recorded at a first set of successive time periods to form a first spatial-temporal image plane and each of the second plurality of images recorded at a second set of successive time periods to form a second spatial-temporal image plane; and
    combining the first spatial-temporal image plane and the second spatial-temporal image plane to form a three-dimensional image of the retina, wherein one dimension is a temporal dimension including a time varying signal representing the flow of blood in the retina.

2. The method of claim 1 wherein each of the spatial-temporal image planes has N spatial pixels captured simultaneously in the line of light at N successive time periods.

3. The method of claim 2 further comprising illuminating the retina with the line of light at N positions to form N spatial-temporal image planes.

4. The method of claim 3 further comprising combining the N spatial-temporal image planes to form an image cube of the retina with dimensions of N×N×N.

5. The method of claim 1 wherein recording a respective plurality of images comprises confocally receiving with a linear array detector light reflected from the portion of the retina illuminated with the line of light.

6. The method of claim 1 further comprising performing a Fourier transform of the three-dimensional image of the retina to extract a power spectrum of each image pixel.

7. The method of claim 6 wherein the power spectrum comprises a AC portion representing blood flow and a DC portion representing average image brightness.

8. The method of claim 7 further comprising normalizing the power spectrum by the DC values to remove variability across a respective plurality of images due to intensity of the line of light or reflectivity of an imaged volume of tissue.

9. The method of claim 6 further comprising binning portions of the power spectrum according to a frequency range.

10. The method of claim 9 wherein a low frequency bin represents perfusion through the micro-vasculature of the retina.

11. The method of claim 9 wherein a middle frequency bin represents blood flow in small retinal vessels.

12. The method of claim 9 wherein a high frequency bin represents blood flow in large retinal vessels.

13. The method of claim 9 further comprising combining a plurality of frequency bins to form a video of blood flow and vessel pattern.

14. The method of claim 6 further comprising scaling binned portions of the power spectrum.

15. The method of claim 14 further comprising scaling binned portions to form a normalized spectrum to compare blood flow in a first patient and blood flow in a second patient.

16. The method of claim 14 further comprising scaling binned portions to form a normalized stretched spectrum to compare blood flow in a patient at a first time and blood flow in the same patient at a second time.

17. An apparatus for monitoring blood flow in a retina, comprising:
a retinal tracking device for locking onto a feature of the retina;
a line-scanning laser ophthalmoscope for illuminating the retina with a line of light at a first position and at a second position, including a linear array detector for confocally receiving a first plurality of images of the line of light on the retina at the first position for a first set of successive time periods and a second plurality of images of the line of light on the retina at the second position for a second set of successive time periods; and
a processor for forming a first spatial-temporal image plane from the first plurality of images of the line of light on the retina at the first position versus the first set of successive time periods, forming a second spatial-temporal image plane from the second plurality of images of the line of light on the retina at the second position versus the second set of successive time periods, and combining the first spatial-temporal image plane and the second spatial-temporal image plane to form a three-dimensional image of the retina, wherein one dimension is a temporal dimension including a time varying signal representing the flow of blood in the retina.

18. The apparatus of claim 17 wherein each of the spatial-temporal image planes has N spatial pixels captured simultaneously in the line of light at N successive time periods.

19. The apparatus of claim 18 wherein the retina is illuminated with the line of light at N positions to form N spatial-temporal image planes.

20. The apparatus of claim 19 wherein the processor combines the N spatial-temporal image planes to form an image cube of the retina with dimensions of N×N×N.

21. The apparatus of claim 17 wherein the processor performs a Fourier transform of the three-dimensional image of the retina to extract a power spectrum of each image pixel.

22. The apparatus of claim 17 wherein the retinal tracking device comprises a confocal reflectometer with a closed loop servo system to look onto a feature of the fundus of the retina.

23. The apparatus of claim 17 wherein the retinal tracking device locks a tracking beam onto a retinal feature and processes the backreflected signal from the tracking beam to stabilize the line-scanning laser ophthalmoscope.

24. The apparatus of claim 17 wherein the retinal tracking device tracks at a rate that exceeds the maximum rate of motion of an eye.

25. The apparatus of claim 24 wherein the retinal tracking device comprises a bandwidth of greater than 1 kHz.

26. The apparatus of claim 17 wherein the retinal tracking device improves the resolution of the line-scanning laser ophthalmoscope.

27. An apparatus for monitoring blood flow in a retina, comprising:
a means for illuminating the retina with a line of light at a first position and a second position;
a means for recording a first plurality of images of the line of light on the retina at the first position and a second plurality of images of the line of light on the retina at the second position, each of the first plurality of images recorded at successive time periods to form a first spatial-temporal image plane and each of the second plurality of images recorded at a respective time period to form a second spatial-temporal image plane; and
a means for combining the first spatial-temporal image plane and the second spatial-temporal image plane to form a three-dimensional image of the retina, wherein one dimension is a temporal dimension including a time varying signal representing the flow of blood in the retina.

* * * * *